United States Patent
Phan et al.

[11] Patent Number: 6,124,269
[45] Date of Patent: Sep. 26, 2000

[54] 2-HALO-6-O-SUBSTITUTED KETOLIDE DERIVATIVES

[75] Inventors: Ly Tam Phan, Park City; Yat Sun Or, Libertyville, both of Ill.; Daniel T. Chu, Santa Clara; Jacob J. Platter, Berkeley, both of Calif.; Yan Chen, Grayslake; Richard F. Clark, Mundelein, both of Ill.

[73] Assignee: Abbott Laboratories, Abbott Park, Ill.

[21] Appl. No.: 09/154,294

[22] Filed: Sep. 16, 1998

Related U.S. Application Data

[60] Provisional application No. 60/063,700, Oct. 29, 1997.

[51] Int. Cl.$^7$ .............................. A61K 31/70; C07H 17/08
[52] U.S. Cl. .............................. 514/29; 536/7.2; 536/7.3; 536/7.4
[58] Field of Search .............................. 514/29; 536/7.2, 536/7.3, 7.4

[56] References Cited

U.S. PATENT DOCUMENTS

| | | | |
|---|---|---|---|
| 4,990,602 | 2/1991 | Morimoto et al. | 536/7.4 |
| 5,403,923 | 4/1995 | Kashimura et al. | 536/7.4 |
| 5,444,051 | 8/1995 | Agouridas et al. | 514/29 |
| 5,631,355 | 5/1997 | Asaka et al. | 536/7.4 |
| 5,747,467 | 5/1998 | Agouridas et al. | 514/29 |
| 5,866,549 | 2/1999 | Or et al. | 514/29 |

FOREIGN PATENT DOCUMENTS

| | | |
|---|---|---|
| 0596802 | 5/1994 | European Pat. Off. |
| 2742757 | 5/1997 | France |
| 2742757 | 6/1997 | France |
| 9209614 | 6/1992 | WIPO |
| 9710251 | 3/1997 | WIPO |
| 9717356 | 5/1997 | WIPO |

OTHER PUBLICATIONS

Journal of Antibiotics, vol. 43, No. 3 (Mar. 1990), pp. 286–294, Morimoto et al., "Chemical Modification of Erythromycins: II. Synthesis and Antibacterial Activity of O–Alkyl Derivatives of Erythromycin A".

Journal of Antibiotics, vol. 37, No. 2 (Feb. 1984), pp. 187–189, Morimoto, et al., "Chemical Modifications of Erythromycins: I. Synthesis and Antibacterial Activity of 6–O–Methylerythromycins A".

*Primary Examiner*—Kathleen K. Fonda
*Attorney, Agent, or Firm*—Mona Anand

[57] ABSTRACT

Novel 2-halo-6-O-substituted ketolide derivatives and pharmaceutically acceptable salts and esters thereof having antibacterial activity having a formula

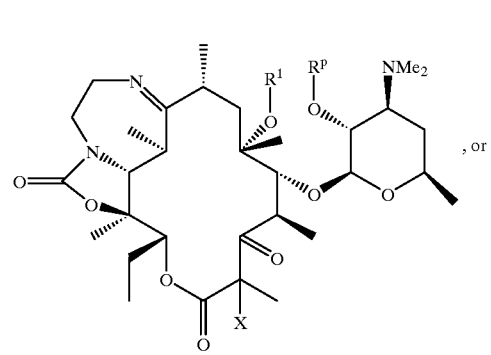

(I)

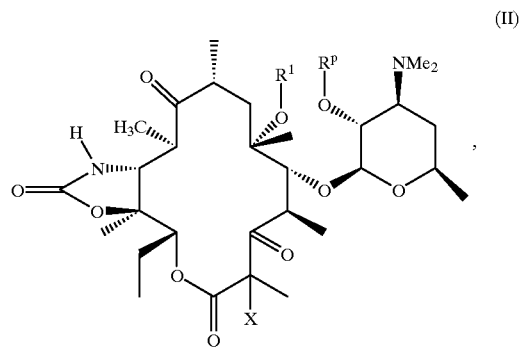

(II)

compositions comprising a therapeutically effective amount of a compound of the invention in combination with a pharmaceutically acceptable carrier, a method for treating bacterial infections by administering to a mammal a pharmaceutical composition containing a therapeutically-effective amount of a compound of the invention, and processes for their preparation.

14 Claims, No Drawings

2-HALO-6-O-SUBSTITUTED KETOLIDE DERIVATIVES

This application claims the benefit of U.S. Provisional Application Ser. No. 60/063,700 filed Oct. 29, 1997.

TECHNICAL FIELD

This invention relates to novel semi-synthetic macrolides having antibacterial activity, to pharmaceutical compositions comprising these compounds, and to a medical method of treatment. More particularly, the invention relates to novel 2-halo-6-O-substituted ketolide derivatives, methods for preparing them, compositions containing these compounds, and a method of treating bacterial infections with such compositions.

BACKGROUND OF THE INVENTION

Erythromycins A through D, represented by formula (E),

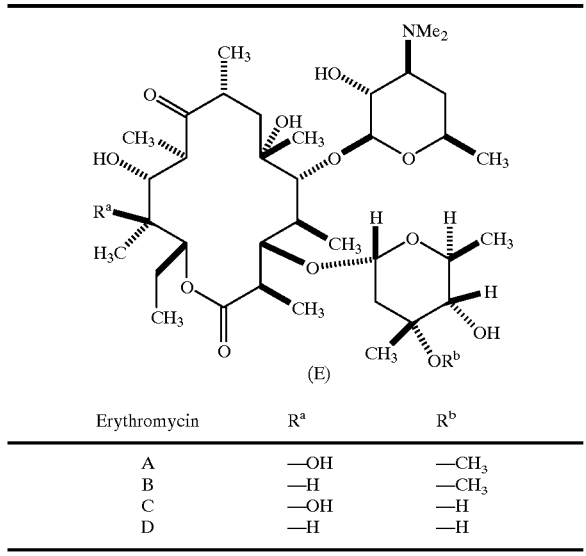

| Erythromycin | $R^a$ | $R^b$ |
|---|---|---|
| A | —OH | —CH$_3$ |
| B | —H | —CH$_3$ |
| C | —OH | —H |
| D | —H | —H | are well-known and potent antibacterial agents, used widely to treat and prevent bacterial infection. As with other antibacterial agents, however, bacterial strains having resistance or insufficient susceptibility to erythromycin have been identified. Also, erythromycin A has only weak activity against Gram-negative bacteria. Therefore, there is a continuing need to identify new erythromycin derivative compounds which possess improved antibacterial activity, which have less potential for developing resistance, which possess the desired Gram-negative activity, or which possess unexpected selectivity against target microorganisms. Consequently, numerous investigators have prepared chemical derivatives of erythromycin in an attempt to obtain analogs having modified or improved profiles of antibiotic activity.

Morimoto et al. describes the preparation of 6-O-methyl erythromycin A in *J. Antibiotics*, 37:187 (1984). Morimoto et al. further discloses 6-O-alkyl erythromycin A derivatives in *J. Antibiotics*, 43: 286 (1990) and in U.S. Pat. No. 4,990,602.

U.S. Pat. No. 5,444,051 discloses certain 6-O-substituted-3-oxoerythromycin A derivatives. PCT application WO 97/10251, published Mar. 20, 1997, discloses intermediates useful for preparation of 6-O-methyl 3-descladinose erythromycin derivatives.

U.S. Pat. No. 5,403,923 discloses certain tricyclic 6-O-methyl erythromycin A derivatives (Asaka, TAISHO) corresponding to PCT application WO 92/09614, published Jun. 11, 1992, and U.S. Pat. No. 5,631,355 discloses certain tricyclic 6-O-methyl 3-oxo erythromycin derivatives. U.S. Pat. No. 5,527,780 discloses certain bicyclic 6-O -methyl-3-oxo erythromycin A derivatives (Agouridas, ROUSSEL) corresponding to EP application 596802, published May 11, 1994.

PCT application WO 97/17356, published May 15, 1997, discloses tricyclic 6-O-methyl erythromycin A derivatives. Certain intermediates to the present invention are disclosed in U.S. patent application Ser. No. 08/888,350 now issued as U.S. Pat. No. 5,866,549.

Certain 6-O-methyl 2-halogenated ketolides are disclosed in FR 2,742,757 published Jun. 27, 1997.

SUMMARY OF THE INVENTION

The present invention provides a novel class of 2-halo-6-O-substituted ketolide derivatives which possess antibacterial activity.

In one aspect of the present invention are compounds, or pharmaceutically acceptable salts and esters thereof, having a formula selected from the group consisting of

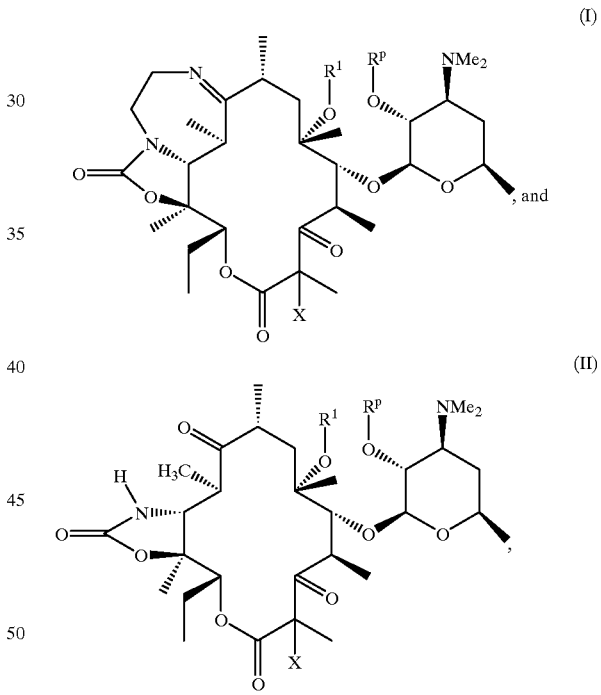

wherein
$R^p$ is hydrogen or a hydroxy protecting group;
X is F, Cl, Br, or I; and
$R^1$ is selected from the group consisting of
(1) $C_1$–$C_6$-alkyl optionally substituted with one or more substituents selected from the group consisting of
  (a) aryl,
  (b) substituted aryl,
  (c) heteroaryl,
  (d) substituted heteroaryl,
  (e) —$NR^3R^4$ wherein $R^3$ and $R^4$ are independently selected from hydrogen and $C_1$–$C_3$-alkyl, or $R^3$ and $R^4$ are taken together with the atom to which they are attached form a 3–7 membered ring containing a moiety selected from the group consisting of —O—, —NH—, —N($C_1$–$C_6$-alkyl-)-, —N(aryl-$C_1$–$C_6$-alkyl-)-, —N(substituted aryl-$C_1$–$C_6$-alkyl-)-, —N(heteroaryl-$C_1$–$C_6$-alkyl-)-, and —N(substituted heteroaryl-$C_1$–$C_6$-alkyl-)-;

(2) —$CH_2$—CH═CH—Y, wherein Y is selected from the group consisting of
(a) H,
(b) aryl,
(c) substituted aryl,
(d) heteroaryl,
(e) substituted heteroaryl;
(f) —CH═$H_2$,
(g) —CH═CH-aryl,
(h) —CH═CH-substituted aryl,
(i) —CH═CH-heteroaryl, and
(j) —CH═CH-substituted heteroaryl,
(k) (aryl)oyl,
(l) (substituted aryl)oyl,
(m) (heteroaryl)oyl, and
(n) (substituted heteroaryl)oyl; and (3) —$CH_2$—C═C—Y, wherein Y is as defined previously, with the proviso that in compounds of formula (II) wherein $R^1$ is selected from option (1) the $C_1$–$C_6$-alkyl group must be substituted.

The present invention also provides pharmaceutical compositions which comprise a therapeutically effective amount of a compound as defined above in combination with a pharmaceutically acceptable carrier.

The invention further relates to a method of treating bacterial infections in a host mammal in need of such treatment comprising administering to a mammal in need of such treatment a therapeutically effective amount of a compound as defined above.

In a further aspect of the present invention, processes are provided for the preparation of 2-halo-6-O-substituted ketolide derivatives of Formulas (I)–(II) above.

DETAILED DESCRIPTION OF THE INVENTION

Definitions

As used throughout this specification and the appended claims, the following terms have the meanings specified.

The terms "$C_1$–$C_3$-alkyl", "$C_1$–$C_6$-alkyl", and "$C_1$–$C_{12}$-alkyl" as used herein refer to saturated, straight- or branched-chain hydrocarbon radicals derived from a hydrocarbon moiety containing between one and three, one and six, and one and twelve carbon atoms, respectively, by removal of a single hydrogen atom. Examples of $C_1$–$C_3$-alkyl radicals include methyl, ethyl, propyl and isopropyl, examples of $C_1$–$C_6$-alkyl radicals include, but are not limited to, methyl, ethyl, propyl, isopropyl, n-butyl, tert-butyl, neopentyl and n-hexyl. Examples of $C_1$–$C_{12}$-alkyl radicals include, but are not limited to, all the foregoing examples as well as n-heptyl, n-octyl, n-nonyl, n-decyl, n-undecyl and n-docecyl.

The term "alkylene" denotes a divalent group derived from a straight or branched chain saturated hydrocarbon by the removal of two hydrogen atoms, for example methylene, 1,2-ethylene, 1,1-ethylene, 1,3-propylene, 2,2-dimethylpropylene, and the like.

The term "$C_2$–$C_{12}$-alkenyl" denotes a monovalent group derived from a hydrocarbon moiety containing from two to twelve carbon atoms and having at least one carbon—carbon double bond by the removal of a single hydrogen atom. Alkenyl groups include, for example, ethenyl, propenyl, butenyl, 1-methyl-2-buten-1-yl, and the like.

The term "$C_2$–$C_{12}$-alkenylene" denotes a divalent group derived from a hydrocarbon moiety containing from two to twelve carbon atoms and having at least one carbon—carbon double bond by the removal of two hydrogen atoms. Alkenylene groups include, for example, 1,1-ethenyl, 1,2-propenyl, 1,4-butenyl, 1-methyl-but-1-en-1,4-yl, and the like.

The term "$C_1$–$C_6$-alkoxy" as used herein refers to an $C_1$–$C_6$-alkyl group, as previously defined, attached to the parent molecular moiety through an oxygen atom. Examples of $C_1$–$C_6$-alkoxy, but are not limited to, methoxy, ethoxy, propoxy, iso-propoxy, n-butoxy, tert-butoxy, neo-pentoxy and n-hexoxy.

The term "$C_1$–$C_3$-alkylamino" as used herein refers to one or two $C_1$–$C_3$-alkyl groups, as previously defined, attached to the parent molecular moiety through a nitrogen atom. Examples of $C_1$–$C_3$-alkylamino include, but are not limited to methylamino, dimethylamino, ethylamino, diethylamino, and propylamino.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heteroaryl compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl" as used herein refers to a mono- or bicyclic carbocyclic ring system radical derived from a hydrocarbon moiety containing one or two aromatic rings, respectively, by removal of a single hydrogen atom. Such aryl radicals include, but are not limited to, phenyl, naphthyl, tetrahydronaphthyl, indanyl, indenyl and the like.

The term "(aryl)oyl" as used herein refers to an aryl group, as defined herein, connected to the parent molecular group through a carbonyl group.

The term "$C_3$–$C_7$-cycloalkyl" denotes a monovalent group derived from a monocyclic or bicyclic saturated carbocyclic ring compound by the removal of a single hydrogen atom. Examples include cyclopropyl, cyclobutyl, cyclopentyl, cyclohexyl, and bicyclo[2.2.1]heptyl.

The terms "halo" and "halogen" as used herein refer to an atom selected from fluorine, chlorine, bromine and iodine.

The term "alkylamino" refers to a group having the structure —NH'R" wherein R' is alkyl, as previously defined, Examples of alkylamnino include methylamino, ethylamino, iso-propylamino and the like.

The term "dialkylamino" refers to a group having the structure —NR'R" wherein R' and R" are independently selected from alkyl, as previously defined. Additionally, R' and R" taken together may optionally be —(CH$_2$)$_k$— where k is an integer of from 2 to 6. Examples of dialkylamino include, dimethylamino, diethylaminocarbonyl, methylethylamino, piperidino, and the like.

The term "haloalkyl" denotes an alkyl group, as defined above, having one, two, or three halogen atoms attached thereto and is exemplified by such groups as chloromethyl, bromoethyl, trifluoromethyl, and the like.

The term "alkoxycarbonyl" represents an ester group; i.e. an alkoxy group, attached to the parent molecular moiety through a carbonyl group such as methoxycarbonyl, ethoxycarbonyl, and the like.

The term "thioalkoxy" refers to an alkyl group as previously defined attached to the parent molecular moiety through a sulfur atom.

The term "carboxaldehyde" as used herein refers to a group of formula —CHO.

The term "carboxy" as used herein refers to a group of formula —CO$_2$H.

The term "carboxamide" as used herein refers to a group of formula —CONHR'R" wherein R' and R" are independently selected from hydrogen or alkyl, or R' and R" taken together may optionally be —(CH$_2$)$_k$— where k is an integer of from 2 to 6.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thiophenyl, furanyl, quinolinyl, isoquinolinyl, quinoxalinyl, naphthyridinyl, and the like. The heteroaryl groups of this invention may also be fused to an adjacent aryl or heteroaryl ring. Examples of these types of ring systems include thieno[2,3-b]pyridyl, 1H-pyrrolo[2,3-b]pyridinyl, 3H-methylimidazo[4,5-b]pyridinyl, and the like.

The term "(heterocycle)oyl" as used herein refers to a heterocycle group, as defined herein, connected to the parent molecular group through a carbonyl group.

The term "heterocycloalkyl" as used herein, refers to a non-aromatic partially unsaturated or fully saturated 3- to 10-membered ring system, which includes single rings of 3 to 8 atoms in size and bi- or tri-cyclic ring systems which may include aromatic six-membered aryl or heteroaryl rings fused to a non-aromatic ring. These heterocycloalkyl rings include those having from one to three heteroatoms independently selected from oxygen, sulfur and nitrogen, in which the nitrogen and sulfur heteroatoms may optionally be oxidized and the nitrogen heteroatom may optionally be quaternized.

Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heteroarylalkyl" as used herein, refers to a heteroaryl group as defined above attached to the parent molecular moiety through an alkylene group wherein the alkylene group is of one to four carbon atoms.

"Hydroxy-protecting group", as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of hydroxy-protecting groups include, but are not limited to, methylthiomethyl, tert-dimethylsilyl, tert-butyldiphenylsilyl, ethers such as methoxymethyl, and esters including acetyl benzoyl, and the like.

The term "ketone protecting group", as used herein, refers to an easily removable group which is known in the art to protect a ketone group against undesirable reactions during synthetic procedures and to be selectively removable. The use of ketone-protecting groups is well known in the art for protecting groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991). Examples of ketone-protecting groups include, but are not limited to, ketals, oximes, O-substituted oximes for example O-benzyl oxime, O-phenylthiomethyl oxime, 1-isopropoxycyclohexyl oxime, and the like.

The term "oxo" denotes a group wherein two hydrogen atoms on a single carbon atom in an alkyl group as defined above are replaced with a single oxygen atom (i.e. a carbonyl group).

The term "N-protecting group" or "N-protected" as used herein refers to those groups intended to protect an amino group against undesirable reactions during synthetic procedures. N-protecting groups comprise carbamates, amides including those containing hetero arylgroups, N-alkyl derivatives, amino acetal derivatives, N-benzyl derivatives, imine derivatives, enamine derivatives and N-heteroatom derivatives. Preferred N-protecting groups are formyl, acetyl, benzoyl, pivaloyl, phenylsulfonyl, benzyl, triphenylmethyl (trityl), t-butyloxycarbonyl (Boc), benzyloxycarbonyl (Cbz), nicotinoyl and the like. Commonly used N-protecting groups are disclosed in T. H. Greene and P. G. M. Wuts, *Protective Groups in Organic Synthesis*, 2nd edition, John Wiley & Sons, New York (1991), which is hereby incorporated by reference.

The term "protected-amino" refers to a amino group protected with a N-protecting group, as defined above, including benzoyl, acetyl, trimethylsilyl, triethylsilyl, methoxymethyl groups, for example.

The term "protected-hydroxy" refers to a hydroxy group protected with a hydroxy protecting group, as defined above, including formyl, acetyl, benzoyl, pivaloyl, phenylsulfonyl, benzyl, triphenylmethyl (trityl), t-butyloxycarbonyl (Boc), and benzyloxycarbonyl (Cbz) groups, for example.

The term "protogenic organic solvent" as used herein refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example:

*Organic Solvents Physical Properties and Methods of Purification*, 4th ed., edited by John A. Riddick et al., Vol. II, in the Techniques of Chemistry Series, John Wiley & Sons, NY, 1986.

The term "substituted aryl" as used herein refers to an aryl group as defined herein substituted by independent replacement of one, two or three of the hydrogen atoms thereon with halo, hydroxy, cyano, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, acylamino, mercapto, nitro, carboxaldehyde, carboxyl, alkoxycarbonyl and carboxamide. In addition, any one substitutent may be an aryl, heteroaryl, or heterocycloalkyl group. Also, substituted aryl groups include tetrafluorophenyl and pentafluorophenyl.

The term "substituted heteroaryl" as used herein refers to a heteroaryl group as defined herein substituted by independent replacement of one, two or three of the hydrogen atoms thereon with —Cl, —Br, —F, —I, —OH, —CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl, carboxamide, N-protected amino, —CH(=N—OH), —CH(=N—NH$_2$), and —CH(=N—N=C(CH$_3$)$_2$). In addition, any one substitutent may be an aryl, heteroaryl, or heterocycloalkyl group.

The term "substituted (aryl)oyl" as used herein refers to a (aryl)oyl group as defined herein substituted by independent replacement of one, two or three of the hydrogen atoms thereon with —Cl, —Br, —F, —I, —OH, —CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl, carboxamide, N-protected amino, —CH(=N—OH), —CH(=N—NH$_2$), and —CH(=N—N=C(CH$_3$)$_2$). In addition, any one substitutent may be an aryl, heteroaryl, or heterocycloalkyl group.

The term "substituted (heteroaryl)oyl" as used herein refers to a (heteroaryl)oyl group as defined herein substituted by independent replacement of one, two or three of the hydrogen atoms thereon with —Cl, —Br, —F, —I, —OH, —CN, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, mercapto, nitro, carboxaldehyde, carboxy, alkoxycarbonyl, carboxamide, N-protected amino, —CH(=N—OH), —CH(=N—NH$_2$), and —CH(=N—N=C(CH$_3$)$_2$). In addition, any one substitutent may be an aryl, heteroaryl, or heterocycloalkyl group.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates.

The term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press, 1987, both of which are incorporated herein by reference.

Preferred Embodiments

In a first embodiment of the invention is a compound having the formula (I). In a preferred embodiment of formula (I), X is F.

In a second embodiment of the invention is a compound having the formula (II). In a preferred embodiment of formula (II), X is F.

In a third embodiment of the invention is a compound having the Formula (II)b

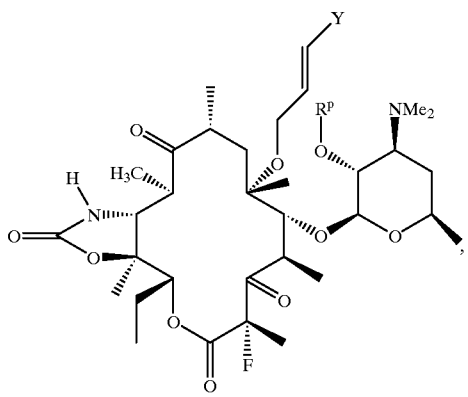

wherein Y and $R^p$ are defined herein.

Representative compounds of the invention are those selected from the group consisting of:

Compound of Formula (I), $R^p$ is H, $R^1$ is methyl, X is F;
Compound of Formula (I), $R^p$ is H, $R^1$ is methyl, X is Cl;
Compound of Formula (I), $R^p$ is H, $R^1$ is methyl, X is Br;
Compound of Formula (II)b, $R^p$ is H, $R^1$ is —CH$_2$-CH=CH—Y, Y is hydrogen, X is F;
Compound of Formula (II)b, $R^p$ is H, $R^1$ is —CH$_2$—CH=CH—Y, Y is (3-quinolyl), X is F;
Compound of Formula (II)b, $R^p$ is H, $R^1$ is —CH$_2$—CH=CH—Y, Y is 6-nitro-3-quinolinyl-, X is F;
Compound of Formula (II)b, $R^p$ is H, $R^1$ is —CH$_2$—CH=CH—Y, Y is phenyl-, X is F;
Compound of Formula (II)b, $R^p$ is H, $R^1$ is —CH$_2$—CH=CH—Y, Y is 6-tert butoxycarbonylamino-3-quinolinyl-, X is F;
Compound of Formula (II)b, $R^p$ is H, $R^1$ is —CH$_2$—CH=CH—Y, Y is 6-amino-3-quinolinyl-, X is F;
Compound of Formula (II)b, $R^p$ is H, $R^1$ is —CH$_2$—CH=CH—Y, Y is 6-quinolinyl-, X is F;
Compound of Formula (II)b, $R^p$ is H, $R^1$ is —CH$_2$—CH=CH—Y, Y is 3-(1,8-naphthyridinyl)-, X is F;
Compound of Formula (II)b, $R^p$ is H, $R^1$ is —CH$_2$—CH=CH—Y, Y is 6-quinoxalinyl-, X is F;
Compound of Formula (II)b, $R^p$ is H, $R^1$ is —CH$_2$—CH=CH—Y, Y is 6-(dimethylamino)-3-quinolinyl-, X is F;
Compound of Formula (II)b, $R^p$ is H, $R^1$ is —CH$_2$—CH=CH—Y, Y is 6-(aminosulfonylmethyl)-3-quinolinyl-, X is F;
Compound of Formula (II)b, $R^p$ is H, $R^1$ is —CH$_2$—CH=CH—Y, Y is 6-(aminocarbonyl)-3-quinolinyl-, X is F;
Compound of Formula (II)b, $R^p$ is H, $R^1$ is —CH$_2$—CH=CH—Y, Y is 6-(N-methylamino)-3-quinolinyl-, X is F;
Compound of Formula (II)b, $R^p$ is H, $R^1$ is —CH$_2$—CH=CH—Y, Y is 6-(formyl)-3-quinolinyl-, X is F;
Compound of Formula (II)b, $R^p$ is H, $R^1$ is —CH$_2$—CH=CH—Y, is 6-[(hydroxyimino)methyl]-3-quinolinyl-, X is F;
Compound of Formula (II)b, $R^p$ is H, $R^1$ is —CH$_2$—CH=CH—Y, Y is 6-[aminoimino(methyl)]-3-quinolinyl-, X is F;
Compound of Formula (II)b, $R^p$ is H, $R^1$ is —CH$_2$—CH=CH—Y, Y is 6-[[(1-methylethylidene)aminoimino]methyl]-3-quinolinyl-, X is F;
Compound of Formula (II)b, $R^p$ is H, $R^1$ is —CH$_2$—CH=CH—Y, Y is 3-(5-cyano)pyridinyl-, X is F;
Compound of Formula (II), $R^p$ is hydrogen, $R^1$ is —CH$_2$—C≡C—Y, Y is hydrogen, X is F;
Compound of Formula (II), $R^p$ is hydrogen, $R^1$ is —CH$_2$—C≡C—Y, Y is phenylcarbonyl-, X is F;
Compound of Formula (II), $R^p$ is hydrogen, $R^1$ is —CH$_2$—C≡C—Y, Y is 2-thienylcarbonyl-, X is F;
Compound of Formula (II), $R^p$ is hydrogen, $R^1$ is —CH$_2$—C≡C—Y, Y is (6-chloro-3-pyridinyl)carbonyl-, X is F;
Compound of Formula (II), $R^p$ is hydrogen, $R^1$ is —CH$_2$—C≡C—Y, Y is 3-quinolinyl-, X is F;
Compound of Formula (II), $R^p$ is hydrogen, $R^1$ is —CH$_2$—C≡C—Y, Y is 3-quinolinyl-, X is F;
Compound of Formula (II), $R^p$ is hydrogen, $R^1$ is —CH$_2$—C≡C—Y, Y is 8-sulfonylamino-3-quinolinyl-, X is F;
Compound of Formula (II), $R^p$ is hydrogen, $R^1$ is —CH$_2$—C≡C—Y, Y is (2,2'-bisthien)-5-yl-, X is F; and
Compound of Formula (II), $R^p$ is hydrogen, $R^1$ is —CH$_2$—C≡C—Y, Y is [5-(2-pyridyl)-2-thienyl]-, X is F.

Antibacterial Activity

In Vitro Assays

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1B demonstrate the antibacterial activity of the compounds of the invention.

Table 1A

Abbreviations of organisms sited in Table 1B

| Microorganism | Organism code |
|---|---|
| *Staphylococcus aureus* ATCC 6538P | AA |
| *Staphylococcus aureus* A5177 | BB |
| *Staphylococcus aureus* A-5278 | CC |
| *Staphylococcus aureus* CMX 642A | DD |
| *Staphylococcus aureus* NCTC10649M | EE |
| *Staphylococcus aureus* CMX 553 | FF |
| *Staphylococcus aureus* 1775 | GG |
| *Staphylococcus epidermidis* 3519 | HH |
| *Enterococcus faecium* ATCC 8043 | II |
| *Streptococcus bovis* A-5169 | JJ |
| *Streptococcus agalactiae* CMX 508 | KK |
| *Streptococcus pyogenes* EES61 | LL |
| *Streptococcus pyogenes* 930 | MM |
| *Streptococcus pyogenes* PIU 2548 | NN |
| *Micrococcus luteus* ATCC 9341 | OO |
| *Micrococcus luteus* ATCC 4698 | PP |
| *Escherichia coli* JUHL | QQ |
| *Escherichia coli* SS | RR |
| *Escherichia coli* DC-2 | SS |
| *Candida albicans* CCH 442 | TT |
| *Mycobacterium smegmatis* ATCC 114 | UU |
| *Nocardia asteroides* ATCC 9970 | VV |
| *Haemophilis influenzae* DILL AMP R | WW |
| *Streptococcus pneumoniae* ATCC 6303 | XX |
| *Streptococcus pneumoniae* GYR 1171 | YY |
| *Streptococcus pneumoniae* 5979 | ZZ |
| *Streptococcus pneumoniae* 5649 | ZZA |

TABLE 1B

Antibacterial Activity (MIC's) of Selected Compounds

| Organism code | Example 1 | Example 2 | Example 3 | Example 4 | Ery. A standard |
|---|---|---|---|---|---|
| AA | 0.1 | 25 | 0.39 | 0.78 | 0.2 |
| BB | 0.1 | 25 | 0.39 | 0.78 | 3.1 |
| CC | >100 | >100 | >100 | >100 | >100 |
| DD | 0.1 | 50 | 0.39 | 0.78 | 0.39 |
| EE | 0.2 | 25 | 0.39 | 0.78 | 0.39 |
| FF | 0.1 | 25 | 0.39 | 0.78 | 0.39 |
| GG | >100 | >100 | >100 | >100 | >100 |
| HH | 0.2 | 25 | 0.39 | 0.78 | 0.39 |
| II | 0.05 | 12.5 | 0.1 | 0.2 | 0.05 |
| JJ | 0.01 | 1.56 | 0.2 | 0.2 | 0.02 |
| KK | 0.02 | 3.1 | 0.2 | 0.2 | 0.05 |
| LL | 0.01 | 3.1 | 0.05 | 0.2 | 0.05 |
| MM | >100 | >100 | >100 | >100 | >100 |
| NN | 0.2 | 6.2 | 0.39 | 0.39 | 6.2 |
| OO | 0.02 | 3.1 | 0.05 | 0.39 | 0.05 |
| PP | 0.2 | 6.2 | 0.39 | 0.78 | 0.2 |
| QQ | >50 | >100 | >100 | >100 | >100 |
| RR | 0.2 | 0.78 | 0.39 | 0.78 | 0.78 |
| SS | 25 | >100 | >100 | >100 | >100 |
| TT | >100 | >100 | >100 | >100 | >100 |
| UU | 0.2 | >100 | 1.56 | 6.2 | 3.1 |
| VV | 0.05 | 50 | 0.39 | 0.39 | 0.1 |
| WW | 2 | 32 | 8 | 8 | 4 |
| XX | 0.03 | 4 | 0.125 | 0.06 | 0.06 |
| YY | 0.03 | 4 | 0.125 | 0.03 | 0.06 |
| ZZ | >128 | >128 | 128 | >128 | >128 |
| ZZA | 0.5 | 4 | 2 | 0.25 | 16 |

| Organism | Example 5 | Example 6 | Example 7 | Example 8 | Ery. A standard |
|---|---|---|---|---|---|
| AA | 0.05 | 0.05 | 0.05 | 0.39 | 0.2 |
| BB | 0.05 | 0.05 | 0.05 | 0.39 | 6.2 |
| CC | >100 | 100 | 100 | >100 | >100 |
| DD | 0.05 | 0.05 | 0.05 | 0.39 | 0.39 |
| EE | 0.05 | 0.1 | 0.05 | 0.39 | 0.39 |
| FF | 0.05 | 0.05 | 0.05 | 0.39 | 0.39 |
| GG | >100 | 100 | 100 | >100 | >100 |
| HH | 0.05 | 0.05 | 0.05 | 0.39 | 0.2 |
| II | 0.02 | 0.05 | 0.02 | 0.2 | 0.05 |
| JJ | 0.005 | 0.01 | ≦0.005 | 0.05 | 0.05 |
| KK | 0.01 | 0.02 | ≦0.005 | 0.05 | 0.05 |
| LL | 0.01 | ≦0.005 | ≦0.005 | 0.05 | 0.02 |
| MM | 0.2 | 0.39 | 25 | 12.5 | >100 |
| NN | 0.05 | 0.05 | 0.05 | 0.39 | 12.5 |
| OO | 0.01 | 0.01 | ≦0.005 | 0.05 | 0.02 |
| PP | 0.1 | 0.05 | 0.02 | 0.39 | 0.39 |
| QQ | 25 | 25 | 50 | >100 | 50 |
| RR | 0.2 | 0.05 | 0.1 | 6.2 | 0.39 |
| SS | 25 | 25 | 25 | >100 | >100 |
| TT | 12.5 | 100 | >100 | >100 | >100 |
| UU | 0.2 | 0.1 | 0.05 | 0.78 | 6.2 |
| VV | 0.005 | 0.02 | ≦0.005 | 0.78 | 0.05 |
| WW | 1 | 2 | 2 | 16 | 4 |
| XX | 0.03 | ≦0.004 | ≦0.004 | 0.06 | 0.125 |
| YY | 0.03 | ≦0.004 | ≦0.004 | 0.06 | 0.06 |
| ZZ | 1 | 1 | 64 | 16 | >128 |
| ZZA | 0.25 | 0.125 | 0.25 | 1 | 16 |

| Organism | Example 9 | Example 10 | Example 11 | Example 12 | Ery. A standard |
|---|---|---|---|---|---|
| AA | 0.02 | 0.1 | 0.05 | 0.05 | 0.2 |
| BB | 0.02 | 0.1 | 0.05 | 0.05 | 6.2 |
| CC | >100 | >100 | >100 | >100 | >100 |
| DD | 0.02 | 0.1 | 0.05 | 0.05 | 0.39 |
| EE | 0.05 | 0.1 | 0.05 | 0.05 | 0.39 |
| FF | 0.02 | 0.1 | 0.05 | 0.05 | 0.39 |
| GG | >100 | >100 | 100 | >100 | >100 |
| HH | 0.02 | 0.2 | 0.05 | 0.05 | 0.2 |
| II | 0.01 | 0.05 | 0.05 | 0.01 | 0.05 |
| JJ | ≦0.005 | 0.01 | 0.01 | ≦0.005 | 0.05 |
| KK | ≦0.005 | 0.05 | 0.01 | 0.01 | 0.05 |
| LL | ≦0.005 | 0.02 | 0.39 | 0.01 | 0.02 |
| MM | 0.2 | 0.39 | 0.1 | 0.2 | >100 |
| NN | 0.1 | 0.1 | 0.01 | 0.05 | 12.5 |
| OO | ≦0.005 | 0.02 | 0.01 | ≦0.005 | 0.02 |
| PP | 0.02 | 0.1 | 0.05 | 0.05 | 0.39 |
| QQ | 25 | 100 | 25 | 12.5 | 50 |
| RR | 0.2 | 0.1 | 0.2 | 0.1 | 0.39 |
| SS | 25 | 100 | 12.5 | 12.5 | >100 |
| TT | >100 | >100 | >100 | >100 | >100 |
| UU | 0.78 | 0.1 | 0.78 | 0.2 | 6.2 |
| VV | <0.005 | 0.01 | 0.01 | ≦0.005 | 0.05 |
| WW | 2 | 2 | 2 | 2 | 4 |
| XX | 0.015 | 0.015 | ≦0.004 | ≦0.004 | 0.125 |
| YY | 0.015 | 0.015 | ≦0.004 | ≦0.004 | 0.06 |
| ZZ | 0.25 | 0.25 | 0.125 | 1 | >128 |
| ZZA | 1 | 0.25 | 0.25 | 0.125 | 16 |

| Organism | Example 13 | Example 14 | Example 15 | Example 16 | Ery. A standard |
|---|---|---|---|---|---|
| AA | 0.2 | 0.05 | 0.05 | 0.05 | 0.2 |
| BB | 0.2 | 0.1 | 0.05 | 0.05 | 6.2 |
| CC | >100 | >100 | >100 | >100 | >100 |
| DD | 0.2 | 0.1 | 0.05 | 0.05 | 0.39 |
| EE | 0.2 | 0.1 | 0.05 | 0.05 | 0.39 |
| FF | 0.2 | 0.1 | 0.05 | 0.05 | 0.39 |
| GG | >100 | >100 | >100 | >100 | >100 |
| HH | 0.2 | 0.1 | 0.05 | 0.05 | 0.2 |
| II | 0.1 | 0.1 | 0.05 | 0.02 | 0.05 |
| JJ | 0.02 | ≦0.005 | 0.01 | ≦0.005 | 0.05 |
| KK | 0.02 | 0.01 | 0.01 | 0.01 | 0.05 |
| LL | 0.05 | 0.01 | 0.01 | 0.01 | 0.02 |
| MM | 0.78 | — | 0.1 | 0.39 | >100 |
| NN | 0.2 | 0.2 | 0.1 | 0.05 | 12.5 |
| OO | 0.02 | 0.01 | 0.01 | 0.01 | 0.02 |
| PP | 0.2 | 0.2 | 0.05 | 0.05 | 0.39 |
| QQ | 50 | 50 | 25 | 50 | 50 |
| RR | 0.78 | 0.1 | 0.2 | 0.2 | 0.39 |
| SS | 100 | 100 | 12.5 | 50 | >100 |
| TT | >100 | >100 | >100 | >100 | >100 |

TABLE 1B-continued

Antibacterial Activity (MIC's) of Selected Compounds

| | | | | | |
|---|---|---|---|---|---|
| UU | 0.78 | 3.1 | 0.39 | 0.39 | 6.2 |
| VV | 0.05 | 0.1 | 0.05 | 0.01 | 0.05 |
| WW | 8 | 2 | 4 | 2 | 4 |
| XX | 0.06 | ≦0.004 | ≦0.004 | 0.03 | 0.125 |
| YY | 0.06 | ≦0.004 | ≦0.004 | 0.03 | 0.06 |
| ZZ | 1 | 2 | 0.5 | 1 | >128 |
| ZZA | 0.5 | 0.25 | 0.25 | 0.25 | 16 |

| Organism | Example 17 | Example 18 | Example 19 | Example 20 | Ery. A standard |
|---|---|---|---|---|---|
| AA | 0.05 | 0.02 | 0.1 | 0.1 | 0.2 |
| BB | 0.1 | 0.05 | 0.2 | 0.1 | 6.2 |
| CC | >100 | 50 | >100 | >100 | >100 |
| DD | 0.1 | 0.05 | 0.2 | 0.1 | 0.39 |
| EE | 0.2 | 0.05 | 0.2 | 0.2 | 0.39 |
| FF | 0.1 | 0.05 | 0.2 | 0.1 | 0.39 |
| GG | >100 | 50 | >100 | >100 | >100 |
| HH | 0.1 | 0.05 | 0.2 | 0.2 | 0.2 |
| II | 0.05 | 0.02 | 0.05 | 0.1 | 0.05 |
| JJ | 0.01 | ≦0.005 | ≦0.005 | 0.01 | 0.05 |
| KK | 0.02 | 0.01 | 0.02 | 0.02 | 0.05 |
| LL | 0.02 | ≦0.005 | 0.02 | 0.02 | 0.02 |
| MM | 0.78 | 0.2 | 1.56 | 1.56 | >100 |
| NN | 0.2 | 0.02 | 0.2 | 0.2 | 12.5 |
| OO | 0.02 | 0.01 | 0.02 | 0.02 | 0.02 |
| PP | 0.05 | 0.02 | 0.1 | 0.1 | 0.39 |
| QQ | 100 | 25 | 100 | >100 | 50 |
| RR | 0.78 | 0.2 | 0.78 | 0.78 | 0.39 |
| SS | 100 | 50 | 100 | >100 | >100 |
| TT | >100 | >100 | >100 | >100 | >100 |
| UU | 0.39 | 0.78 | 0.78 | 0.78 | 6.2 |
| VV | 0.02 | 0.01 | 0.02 | 0.02 | 0.05 |
| WW | 2 | 2 | 2 | 4 | 4 |
| XX | 0.03 | 0.015 | 0.06 | 0.125 | 0.125 |
| YY | 0.015 | 0.015 | 0.06 | 0.06 | 0.06 |
| ZZ | 1 | 0.25 | 1 | 2 | >128 |
| ZZA | 0.5 | 0.25 | 0.5 | 1 | 16 |

| Organism | Example 23 | Example 24 | Example 25 | Example 26 | Ery. A standard |
|---|---|---|---|---|---|
| AA | 1.56 | 1.56 | 0.39 | 0.05 | 0.2 |
| BB | 0.78 | 1.56 | 0.39 | 0.05 | 6.2 |
| CC | >100 | >100 | >100 | >100 | >100 |
| DD | 1.56 | 1.56 | 0.39 | 0.05 | 0.39 |
| EE | 1.56 | 1.56 | 0.78 | 0.1 | 0.39 |
| FF | 0.78 | 1.56 | 0.39 | 0.05 | 0.39 |
| GG | >100 | >100 | >100 | >100 | >100 |
| HH | 1.56 | 1.56 | 0.39 | 0.05 | 0.2 |
| II | 0.78 | 0.39 | 0.2 | 0.02 | 0.05 |
| JJ | 0.1 | 0.2 | 0.1 | 0.01 | 0.05 |
| KK | 0.39 | 0.39 | 0.1 | 0.02 | 0.05 |
| LL | 0.39 | 0.39 | 0.1 | 0.02 | 0.02 |
| MM | >100 | 100 | 6.2 | 0.1 | >100 |
| NN | 1.56 | 3.1 | 0.39 | 0.05 | 12.5 |
| OO | 0.2 | 0.2 | 0.2 | 0.02 | 0.02 |
| PP | 1.56 | 0.78 | 0.39 | 0.05 | 0.39 |
| QQ | >100 | 100 | >100 | 25 | 50 |
| RR | 3.1 | 3.1 | 3.1 | 0.2 | 0.39 |
| SS | >100 | >100 | >100 | 25 | >100 |
| TT | >100 | >100 | >100 | >100 | >100 |
| UU | 3.1 | 3.1 | 0.78 | 0.2 | 6.2 |
| VV | 0.78 | 0.78 | 0.2 | 0.01 | 0.05 |
| WW | 8 | 16 | 2 | 2 | 4 |
| XX | 0.03 | 0.06 | ≦0.004 | ≦0.004 | 0.125 |
| YY | 0.03 | 0.03 | ≦0.004 | ≦0.004 | 0.06 |
| ZZ | >128 | >64 | 0.06 | 16 | >128 |
| ZZA | 2 | 1 | 0.06 | 0.25 | 16 |

| Organism | Example 27 | Example 28 | Ery. A standard |
|---|---|---|---|
| AA | 0.1 | 0.05 | 0.2 |
| BB | 0.1 | 0.1 | 6.2 |
| CC | 50 | >100 | >100 |
| DD | 0.1 | 0.1 | 0.39 |

TABLE 1B-continued

Antibacterial Activity (MIC's) of Selected Compounds

| | | | |
|---|---|---|---|
| EE | 0.1 | 0.2 | 0.39 |
| FF | 0.1 | 0.1 | 0.39 |
| GG | 25 | >100 | >100 |
| HH | 0.1 | 0.1 | 0.2 |
| II | 0.02 | 0.05 | 0.05 |
| JJ | ≦0.005 | 0.01 | 0.05 |
| KK | 0.01 | 0.02 | 0.05 |
| LL | 0.01 | 0.02 | 0.02 |
| MM | 0.78 | 0.78 | >100 |
| NN | 0.1 | 0.2 | 12.5 |
| OO | ≦0.005 | 0.02 | 0.02 |
| PP | 0.1 | 0.05 | 0.39 |
| QQ | 100 | 100 | 50 |
| RR | 0.2 | 0.78 | 0.39 |
| SS | >100 | 100 | >100 |
| TT | >100 | >100 | >100 |
| UU | 0.2 | 0.39 | 6.2 |
| VV | 0.02 | 0.02 | 0.05 |
| WW | 4 | 2 | 4 |
| XX | 0.015 | ≦0.004 | 0.125 |
| YY | 0.015 | ≦0.004 | 0.06 |
| ZZ | 0.5 | 16 | >128 |
| ZZA | 0.125 | 0.25 | 16 |

TABLE 1C

The Effect of a 2-Halo Substituent on the In Vitro Antibacterial Activity (MIC's) of Selected Compounds of Formula (I), RP is H, $R^1$ is methyl

| Organism | Standard (X is H) | Example 1 (X is F) | Example 2 (X is Cl) | Example 3 (X is Br) |
|---|---|---|---|---|
| AA | 0.2 | 0.1 | 25 | 0.78 |
| BB | 0.2 | 0.1 | 25 | 0.78 |
| CC | >100 | >100 | >100 | >100 |
| LL | 0.02 | 0.03 | 4 | <0.125 |
| MM | >100 | >128 | 128 | 128 |
| NN | 0.39 | 0.5 | 16 | 4/32 |
| WW | 4 | 2 | 32 | 8 |
| XX | 0.06 | 0.03 | 4 | 0.25 |
| ZZ | >128 | >128 | >128 | >128 |
| ZZA | 0.5 | 0.5 | 4 | 1 |

As shown in Table 1C, introduction of fluoride to the 2-position of ketolides to produce compounds of Formula I provides surprising improved inhibitory activity when compared to compounds wherein X is hydrogen, Br, or Cl.

TABLE 1D

The Effect of 2-H versus 2-F Substitution on the In Vitro
Antibacterial Activity (MIC's) of Selected Compounds of Formula (II)b

| Organism | Standard A (X is H) | Example 5 (X is F) | Standard B (X is H) | Example 7 (X is F) | Standard C (X is H) | Example 12 (X is F) |
|---|---|---|---|---|---|---|
| LL | 0.03 | 0.03 | 0.03 | ≦0.04 | 0.03 | ≦0.04 |
| MM | 1 | 0.25 | 64 | 16 | 1 | 0.5 |
| NN | 0.25 | 0.25 | 0.25 | 0.25 | 0.25 | 0.125 |
| WW | 2 | 1 | 4 | 2 | 2 | 2 |
| XX | 0.03 | 0.03 | 0.03 | ≦0.04 | 0.015 | ≦0.004 |
| ZZ | 16 | 1 | 128 | 64 | 64 | 1 |
| ZZA | 0.25 | 0.25 | 0.25 | 0.25 | 0.5 | 0.125 |

As shown in Table 1D, introduction of fluoride to the 2-position of ketolides produces surprising improved inhibitory activity when compared to the corresponding compounds wherein X is hydrogen (Standards A, B, and C).

In Vivo Assays

Representative compounds of the present invention were assayed in vivo for antibacterial activity as follows:

Mouse Protection Test

The efficacy of tricyclic ketolides was evaluated in mouse models of acute bacterial infections. Female CF-1 mice weighing 20–28 g were inoculated intraperitoneally with 24 hour cultures of *S. aureus* NCTC 10649 or *S. pneumoniae* AC6303 adjusted to yield approximately 100 times the 50% lethal dose ($LD_{50}$). Concurrently with each trial, the challenge $LD_{50}$ was validated by inoculation of untreated mice with log dilutions of the bacterial inoculum. A 5-log dilution range of the bacterial challenges was inoculated into five groups of 10 mice each (10 mice per log dilution). A mortality rate of 100% was produced in all groups of untreated mice with the 100×$LD_{50}$. Test compounds were formulated in 2% ethanol in PBS and administered orally by gavage or subcutaneously at 1 hour and 5 hours post-infection. Mortality was assessed for 7 days, and the mean effective doses needed to protect 50% of the mice ($ED_{50}$) was calculated from the cumulative mortality by trimmed-logit analysis.

*H. influenzae* Lung Infection

The efficacy of tricyclic ketolides was evaluated in a mouse model of *H. influenzae* pulmonary infection. *H. influenzae* 1435 was grown overnight in BHI. Normal, non-immunosuppressed female CF-1 mice weighing 20–26 g were inoculated intranasally with 100 microliters of broth containing approximately $4.0 \times 10^6$ cfu of *H. influenzae*. Compounds were administered 1, 12, 24 and 36 hours post infection by oral dosing (gavage) or subcutaneous injection. Bacterial burden was determined 48 hours post infection by dilution plating of lung tissue on chocolate agar. Therapeutic dose was established by determining the dosage which produced a ≧2 log reduction in bacterial burden (compared to untreated controls) in ≧70% of the mice. The results of these assays are shown in Table 1E.

TABLE 1E

The Effect of 2-F Substitution on the In Vivo Antibacterial Activity
(MIC's) of Formula (I), $R^p$ is hydrogen, $R^1$ is methyl

| Organism | X is H | X is F |
|---|---|---|
| *Staphylococcus aureus* | 13 | 9.4 |
| *Haemophilis influenzae* | 10 | 7.2 |
| *Streptococcus pneumoniae* | >60 | 35.9 |

TABLE 1F

The Effect of 2-F Substitution on the In Vivo Antibacterial Activity
(MIC's) of Formula (II)b, $R^p$ is hydrogen, $R^1$ is 6-quinolinyl-

| Organism | X is H | X is F |
|---|---|---|
| *Staphylococcus aureus* | — | <6.5 |
| *Streptococcus pneumoniae* | 25.9 | 5.5 |

As shown in Tables 1E and 1F, introduction of fluoride to the 2-position of ketolides produces surprising improved in vivo inhibitory activity when compared to the corresponding compounds wherein X is hydrogen.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar—agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 2000 mg of the compound(s) of this invention per day in single or multiple doses.

The process for preparing a compound having the formula

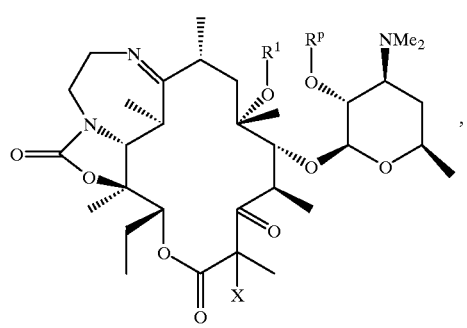

(I)

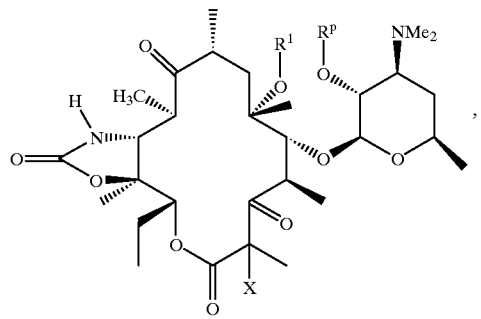

(II)

wherein $R^p$ is hydrogen or a hydroxy protecting group;

X is F, Cl, Br, or I; and $R^1$ is selected from the group consisting of
(1) $C_1$–$C_6$-alkyl optionally substituted with one or more substituents selected from the group consisting of
  (a) aryl,
  (b) substituted aryl,
  (c) heteroaryl,
  (e) —$NR^3R^4$ wherein $R^3$ and $R^4$ are independently selected from hydrogen and $C_1$–$C_3$-alkyl, or $R^3$ and $R^4$ are taken together with the atom to which they are attached form a 3–7 membered ring containing a moiety selected from the group consisting of —O—, —NH—, —N($C_1$–$C_6$-alkyl-)-, —N(aryl-$C_1$–$C_6$-alkyl-)-, —N(substituted aryl-$C_1$–$C_6$-alkyl-)-, —N(heteroaryl-$C_1$–$C_6$-alkyl-)-, and —N(substituted heteroaryl-$C_1$–$C_6$-alkyl-)-;
(2) —$CH_2$–CH=CH—Y, wherein Y is selected from the group consisting of
  (a) H.
  (b) aryl,
  (c) substituted aryl,
  (d) heteroaryl,
  (e) substituted heteroaryl;
  (f) —CH=$H_2$.
  (g) —CH=CH-aryl,
  (h) —CH=CH-substituted aryl,
  (i) —CH=CH-heteroaryl, and
  (c) —CH=CH-substituted heteroaryl,
  (k) (aryl)oyl,
  (l) (substituted aryl)oyl,
  (m) (heteroaryl)oyl, and
  (n) (substituted heteroaryl)oyl; and
(3) —$CH_2$—C≡C—Y, wherein Y is as defined previously, with the proviso that in compounds of formula (II) wherein $R^1$ is selected from option (1) the $C_1$–$C_6$-alkyl group must be substituted, Comprises (a) treating a compound selected from the group consisting of

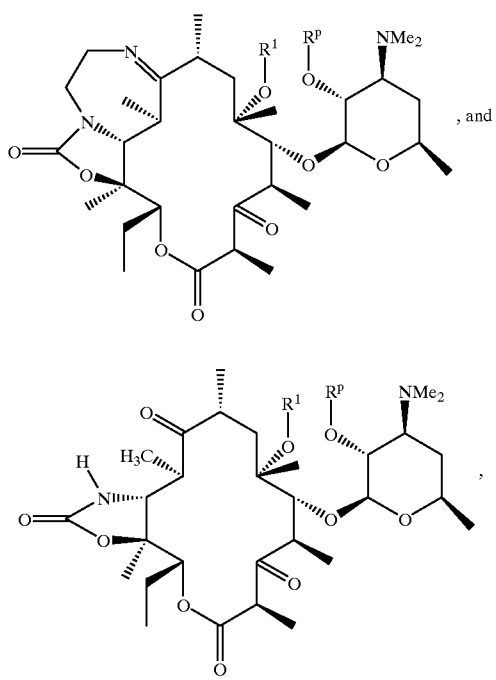

respectively, with a halogenating reagent, and optionally deprotecting.

In a preferred method of the process described above, the halogenating reagent is selected from the group consisting of N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base, hexachloroethane in the presence of base, $CF_3CF_2CH_2ICl_2$, $SO_2Cl_2$, $SOCl_2$, $CF_3SO_2Cl$ in the presence of base, $Cl_2$, NaOCl in the presence of acetic acid, $Br_2$•pyridine•HBr, Br2/acetic acid, N-bromosuccinimide in the presence of base, LDA/BrCH$_2$CH$_2$Br, LDA/CBr$_4$, N-Iodosuccinimide in the presence of base, and $I_2$.

In a preferred method of the process described above, the product is of formula (I), X is F and the halogenating reagent is N-fluorobenzenesulfonimide in the presence of sodium hydride.

In another preferred method of the process described above, the product is of formula (II), X is F and the halogenating reagent is N-fluorobenzenesulfonimide in the presence of sodium hydride. In a more preferred method, the product is of formula (II), X is F, $R^1$ is —CH$_2$—CH=CH—Y and Y is (3-quinolyl), and the halogenating reagent is N-fluorobenzenesulfonimide in the presence of sodium hydride.

Abbreviations

Abbreviations which have been used in the descriptions of the scheme and the examples that follow are: DMF for dimethylformamide; LDA for lithium diisopropylamide; MeOH for methanol; THF for tetrahydrofuran; and triflate for trifluoromethanesulfonate.

Synthetic Methods

The compounds and processes of the present invention will be better understood in connection with the Schemes 1–4 which illustrate the methods by which the compounds of the invention may be prepared. The compounds of the present invention are prepared by the representative methods described below. The groups X, $R^P$, and $R^1$ are as defined previously. Schemes 1–4 are shown following the text section below.

The preparation of the compounds of the invention of formula (I)–(II) from erythromycin A is outlined in Schemes 1–5. The preparation of protected erythromycin A is described in the following United States patents, U.S. Pat. Nos. 4,990,602; 4,331,803, 4,680,368, and 4,670,549 which are incorporated by reference. Also incorporated by reference is European Patent Application EP 260,938.

As shown in Scheme 1, the C-9-carbonyl group of compound 1 is protected with an oxime to give the compound 2, wherein V is =N—O—$R^a$ or =N—O—C($R^b$)($R^c$)—O—$R^a$ where $R^a$ is selected from the group consisting of unsubstituted $C_1$–$C_{12}$-alkyl, $C_1$–$C_{12}$-alkyl substituted with aryl, $C_1$–$C_{12}$-alkyl substituted with substituted aryl, $C_1$–$C_{12}$-alkyl substituted with heteroaryl, $C_1$–$C_{12}$-alkyl substituted with substituted heteroaryl, $C_3$–$C_{12}$-cycloalkyl, —Si—(R*)(R)(R*) wherein R*, R and R* are each independently selected from $C_1$–$C_{12}$-alkyl, and —Si—(aryl)$_3$, and $R^b$ and $R^c$ are each independently selected from the group consisting of (a) hydrogen, (b) unsubstituted $C_1$–$C_{12}$-alkyl, (c) $C_1$–$C_{12}$-alkyl substituted with aryl, and (d) $C_1$–$C_{12}$-alkyl substituted with substituted aryl, or $R^b$ and $R^c$ taken together with the carbon to which they are attached form a $C_3$–$C_{12}$-cycloalkyl ring. An especially preferred carbonyl protecting group V is O-(1-isopropoxycyclohexyl) oxime.

The 2'- and 4"-hydroxy groups of 2 are protected by reaction with a suitable hydroxy protecting reagent, such as those described by T. W. Greene and P. G. M. Wuts in *Protective Groups in Organic Synthesis*, 2nd ed., John Wiley & Son, Inc., 1991, which is incorporated by reference. Hydroxy protecting group reagents include, for example, acetic anhydride, benzoic anhydride, benzyl chloroformate, hexamethyldisilazane, or a trialkylsilyl chloride in an aprotic solvent. Examples of aprotic solvents are dichloromethane, chloroform, tetrahydrofuran (THF), N-methyl pyrrolidinone, dimethylsulfoxide, diethylsulfoxide, N,N-dimethylformamide (DMF), N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof. Protection of 2'- and 4"-hydroxy groups of 2 may be accomplished sequentially or simultaneously to provide compound 3 where $R^P$ is a hydroxy protecting group. Preferred $R^P$ protecting groups include acetyl, benzoyl and trimethylsilyl.

The 6-hydroxy group of compound 3 is then alkylated by reaction with an alkylating agent in the presence of base to give compound 4. Alkylating agents include alkyl chlorides, bromides, iodides or alkyl sulfonates. Specific examples of alkylating agents include allyl bromide, propargyl bromide, benzyl bromide, 2-fluoroethyl bromide, 4-nitrobenzyl bromide, 4-chlorobenzyl bromide, 4-methoxybenzyl bromide, α-bromo-p-tolunitrile, cinnamyl bromide, methyl 4-bromocrotonate, crotyl bromide, 1-bromo-2-pentene, 3-bromo-1-propenyl phenyl sulfone, 3-bromo-1-trimethylsilyl-1-propyne, 3-bromo-2-octyne, 1-bromo-2-butyne, 2-picolyl chloride, 3-picolyl chloride, 4-picolyl chloride, 4-bromomethyl quinoline, bromoacetonitrile, epichlorohydrin, bromofluoromethane, bromonitromethane, methyl bromoacetate, methoxymethyl chloride, bromoacetamide, 2-bromoacetophenone, 1-bromo-2-butanone, bromochloromethane, bromomethyl phenyl sulfone, 1,3-dibromo-1-propene, and the like. Examples of alkyl sulfonates are: allyl O-tosylate, 3-phenylpropyl-O-trifluoromethane sulfonate, n-butyl -O-methanesulfonate and the like. Examples of the solvents used are aprotic solvents such as dimethylsulfoxide, diethylsulfoxide, N,N-dimethylformamide, N,N-dimethylacetamide, N-methyl-2-pyrrolidone, hexamethylphosphoric triamide, a mixture thereof or a mixture of one of these solvents with ether, tetrahydrofuran, 1,2-dimethoxyethane, acetonitrile, ethyl acetate, acetone and the like. Examples of the base which can be used include potassium hydroxide, cesium hydroxide, tetraalkylammonium hydroxide, sodium hydride, potassium hydride, potassium isopropoxide, potassium tert-butoxide, potassium isobutoxide and the like.

The deprotection of the 2'- and 4"-hydroxyl groups is then carried out according to methods described in literature, for example, by T. W. Greene and P. G. M. Wuts in *Protective Groups in Organic Synthesis*, 2nd ed., John Wiley & Son, Inc., 1991, which is incorporated herein by reference. The conditions used for the deprotection of the 2'- and 4"-hydroxyl groups usually results in the conversion of X to =N—OH. (For example, using acetic acid in acetonitrile and water results in the deprotection of the 2'- and 4"-hydroxyl groups and the conversion of X from =N—O—$R^a$ or =N—O—C($R^b$)($R^c$)—O—$R^a$ where $R^a$, $R^b$ and $R^c$ are as defined above to =N—OH). If this is not the case, the conversion is carried out in a separate step.

The deoximation reaction can be carried out according to the methods described in the literature, for example by Greene (op. cit.) and others. Examples of the deoximating agent are inorganic sulfur oxide compounds such as sodium hydrogen sulfite, sodium pyrosulfate, sodium thiosulfate, sodium sulfate, sodium sulfite, sodium hydrosulfite, sodium metabisulfite, sodium dithionate, potassium thiosulfate, potassium metabisulfite and the like. Examples of the solvents used are protic solvents such as water, methanol, ethanol, propanol, isopropanol, trimethylsilanol or a mixture of one or more of the mentioned solvents and the like. The deoximation reaction is more conveniently carried out in the presence of an organic acid such as formic acid, acetic acid and trifluoroacetic acid. The amount of acid used is from about 1 to about 10 equivalents of the amount of compound 5 used. In a preferred embodiment, the deoximation is carried out using an organic acid such as formic acid in ethanol and water to give the desired 6-O-substituted erythromycin compound 6, wherein $R^1$ is as defined previously. In preferred processes of this invention, $R^1$ is methyl or allyl in compound 6.

Scheme 2 illustrates the methods used to prepare intermediate compounds of the invention. The 6-O-substituted compound 6 may be converted to a hydroxy-protected compound 7 by procedures referenced previously.

Compound 7 is treated by mild aqueous acid hydrolysis or by enzymatic hydrolysis to remove the cladinose moiety and give compound 8. Representative acids include dilute hydrochloric acid, sulfuric acid, perchloric acid, chloroacetic acid, dichloroacetic acid or trifluoroacetic acid. Suitable solvents for the reaction include methanol, ethanol, isopropanol, butanol, acetone and the like. Reaction times are typically 0.5 to 24 hours. The reaction temperature is preferably -10 to 60° C.

Compound 8 may be converted to compound 9 by oxidation of the 3-hydroxy group to an oxo group using a Corey-Kim reaction with N-chlorosuccinimide-dimethyl sulfide, or with a modified Swern oxidation procedure using carbodiimide-dimethylsulfoxide. In a preferred reaction, 8 is added into a pre-formed N-chlorosuccinimide and dimethyl sulfide complex in a chlorinated solvent such as methylene chloride at -10 to 25° C. After stirring for about 0.5 to about 4 hours, a tertiary amine such as triethylamine or Hunig's base is added to produce the ketone 9.

Compounds 9 can then treated with an excess of sodium hexamethyldisilazide or a hydride base in the presence of carbonyldiimidazole in an aprotic solvent for about 8 to about 24 hours at about -30° C. to room temperature to give compounds 10. The hydride base may be, for example, sodium hydride, potassium hydride, or lithium hydride, and the aprotic solvent may be one as defined previously. The reaction may require cooling or heating from about -20° C. to about 70° C., depending on the conditions used, and preferably from about 0° C. to about room temperature. The reaction requires about 0.5 hours to about 10 days, and preferably about 10 hours to 2 days, to complete. Portions of this reaction sequence follow the procedure described by Baker et al., *J. Org. Chem.*, 1988, 53, 2340, which is incorporated herein by reference.

Alternately, compounds 7 can be treated with base in the presence of carbonyldlimidazole as described above to give compounds 11, which can then be converted to compounds 12 or 13 in Scheme 3 by forming the cyclic carbamate prior to removal of the cladinose.

Scheme 3 illustrates several routes for the preparation of compounds of formulas (I) and (II). One skilled in the art will be able to easily decide which approach is to be utilized, depending upon the product that is desired.

In one route, compound 10 can be reacted with ethylene diamine in a suitable solvent such as aqueous acetonitrile, DMF or aqueous DMF, and cyclized by treatment of the intermediate (not shown) with dilute acid, such as acetic acid or HCl in a suitable organic solvent such as ethanol or propanol to give compound 12.

In another route, compound 10 can be reacted with aqueous ammonia which results in formation of the cyclic carbamate compound 13.

Scheme 3 also describes representative examples of further elaboration of the 6-position moiety of the compounds of the invention. The desired 6-O-substituted compound may be prepared directly as described above or obtained from chemical modification of an initially prepared 6-O-substituted compound.

For example, compound 13A, where $R^1$ is 6-O-allyl, may be reacted with an aryl halide, a substituted aryl halide, a heteroaryl halide or a substituted heteroaryl halide, under Heck conditions in the presence of (Pd(II) or Pd(O), phosphine, and amine or inorganic base (see *Organic Reactions*, 1982, 27, 345–390), to give the compound 14, wherein Y is aryl, substituted aryl, heteroaryl, and substituted heteroaryl.

Alternately, compound 13A, where $R^1$ is 6-O-allyl, may be reacted with an unsaturated halide reagent selected from the group having the formula halogen-CH=CH-aryl, halogen-CH=CH-substituted aryl, halogen-CH=CH-heteroaryl, and halogen-CH=CH-substituted heteroaryl under Heck conditions in the presence of (Pd(II) or Pd(O), phosphine, and amine or inorganic base, to give the compound 14, wherein Y is aryl, substituted aryl, heteroaryl, substituted heteroaryl, —CH=CH-aryl, —CH=CH-substituted aryl, —CH=CH-heteroaryl, or —CH=CH-substituted heteroaryl.

In another alternate process, the compound where $R^1$ is 6-O—$CH_2$—CH=CH—CH=$H_2$ can be prepared via Scheme 1 by use of 1-bromo-2,4-pentadiene in place of allyl bromide. This allows for preparation of compounds 14 wherein $R^1$ is —$CH_2$—CH=CH—CH=$CH_2$. In turn this compounds may be reacted with an aryl halide, a substituted aryl halide, a substituted aryl halide, a heteroaryl halide or a substituted heteroaryl halide, under Heck conditions to give the compound 14, wherein Y is —CH=CH-aryl, —CH=CH-substituted aryl, —CH=CH-heteroaryl, or —CH=CH-substituted heteroaryl.

Also in Scheme 3, compound 13B, wherein $R^1$ is propargyl, can be treated with an aryl halide, a substituted aryl halide, a heteroaryl halide, a substituted heteroaryl halide, or an unsaturated halide reagent selected from the group having the formula halogen-CH=CH-aryl, halogen-CH=CH-substituted aryl, halogen-CH=CH-heteroaryl, and halogen-CH=CH-substituted heteroaryl in the presence of Pd(triphenylphosphine)$_2$Cl$_2$ and CuI in the presence of an organic amine, such as triethylamine, to give the compound 15, wherein Y is aryl, substituted aryl, heteroaryl, or substituted heteroaryl, —CH=$CH_2$, —CH=CH-aryl, —CH=CH-substituted aryl, —CH=CH-heteroaryl, or —CH=CH-substituted heteroaryl. Compound 15 can be further selectively reduced to the corresponding cis-olefin compound 14 by catalytic hydrogenation in ethanol at atmospheric pressure in the presence of 5% Pd/BaSO$_4$ and quinoline (Rao et al., *J. Org. Chem.*, (1986), 51: 4158–4159). Also in Scheme 3, compound 13B, wherein $R^1$ is propargyl, can be treated with an optionally substituted heteroaryl acid halide or an optionally substituted aryl acid halide using the conditions discussed above to provide compound 15 wherein Y is substituted or unsubstituted (aryl)oyl or (heteroaryl)oyl.

Alternately, compound 13B may also be treated with a boronic acid derivative HB(OR$^{zz}$), wherein R$^{zz}$ is H or $C_1$–$C_6$-alkyl, in an aprotic solvent at 0° C. to ambient temperature to give boronic ester compounds (not shown) which can be treated then with Pd(triphenylphosphine)4 and an aryl halide, a substituted aryl halide, an heteroaryl halide or substituted heteroaryl halide under Suzuki reaction conditions to give additional substituted compounds 14.

Also in Scheme 5, compound 13B, wherein $R^1$ is propargyl, can be treated with an optionally substituted heteroaryl acid halide or an optionally substituted aryl acid halide to provide compound 15 wherein Y is substituted or unsubstituted (aryl)oyl or (heteroaryl)oyl.

Scheme 1

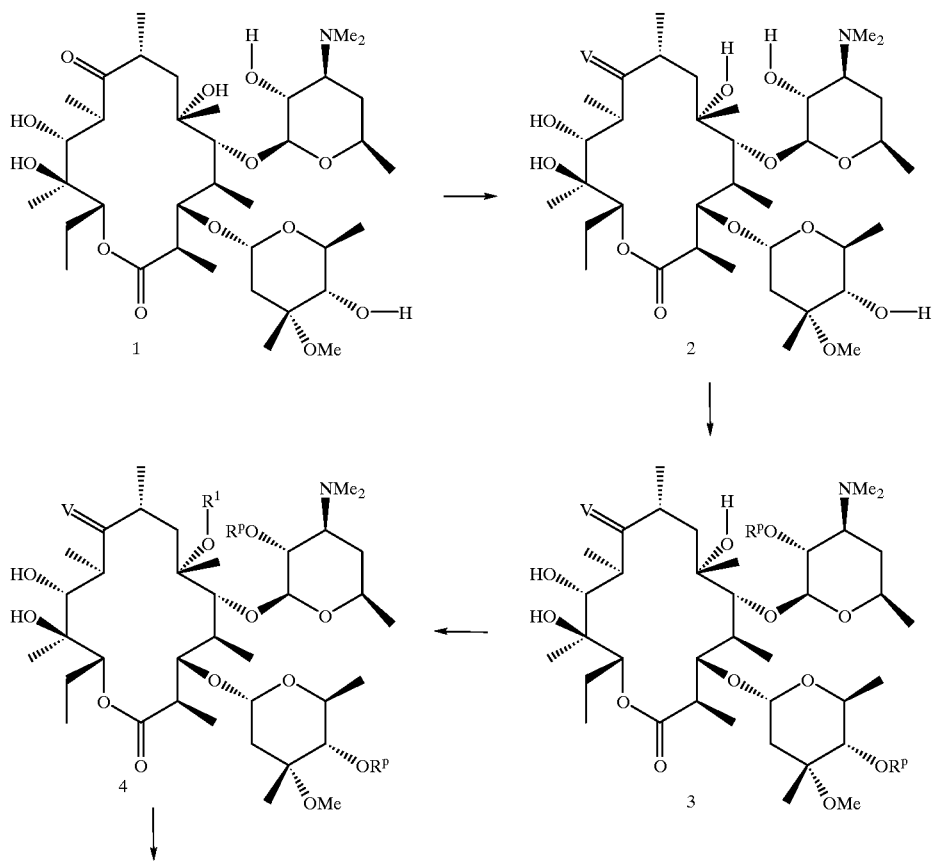

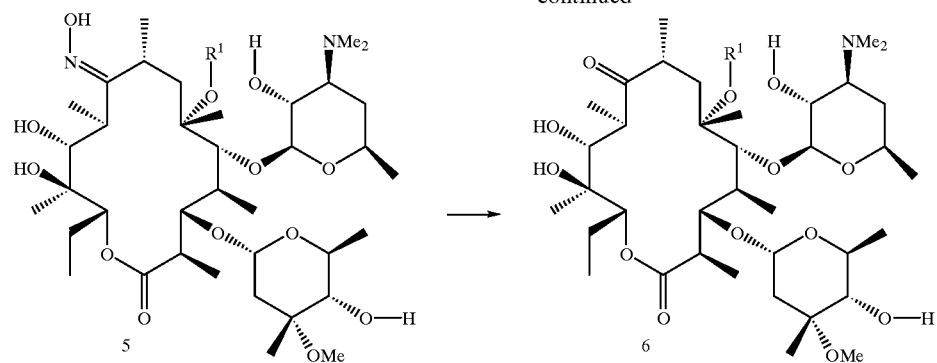
Scheme 2
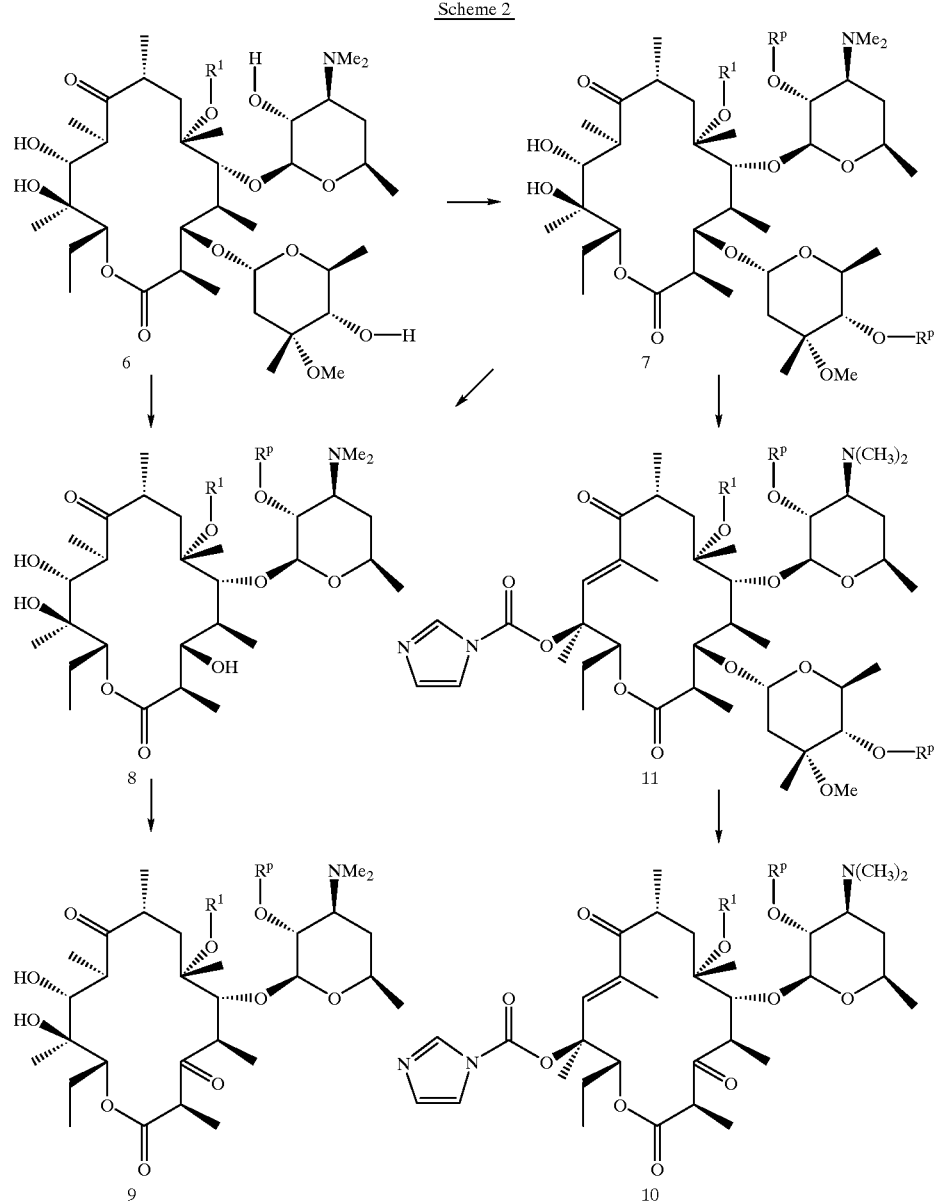

Scheme 3
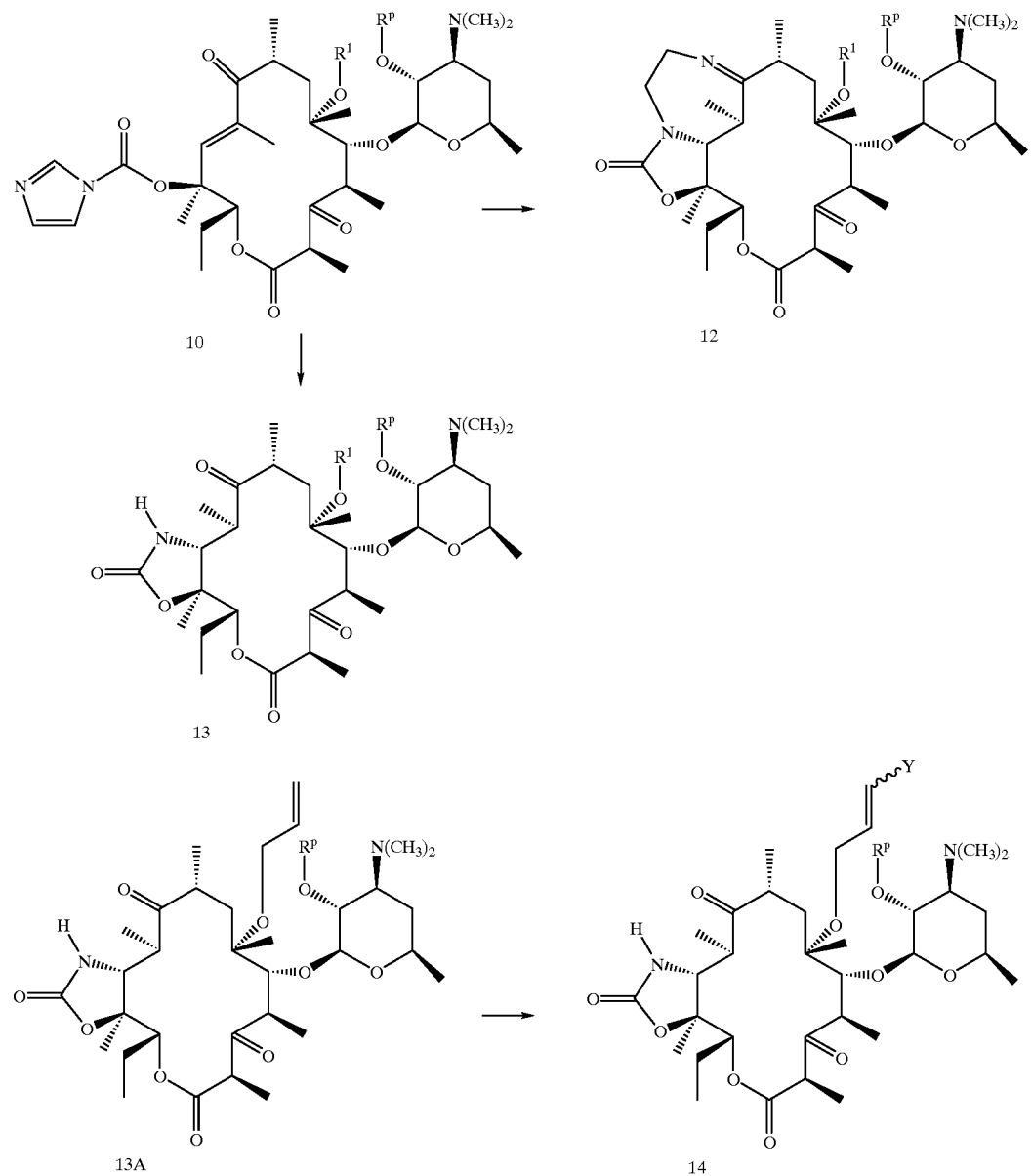

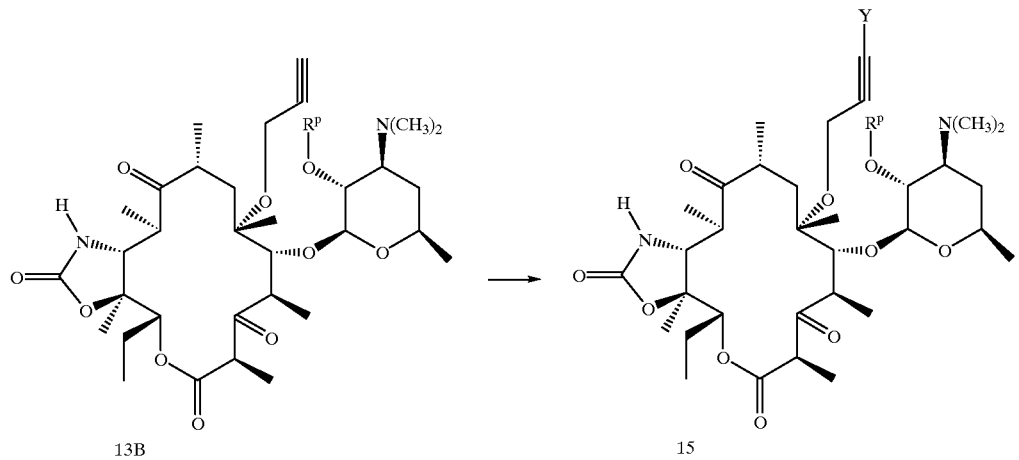

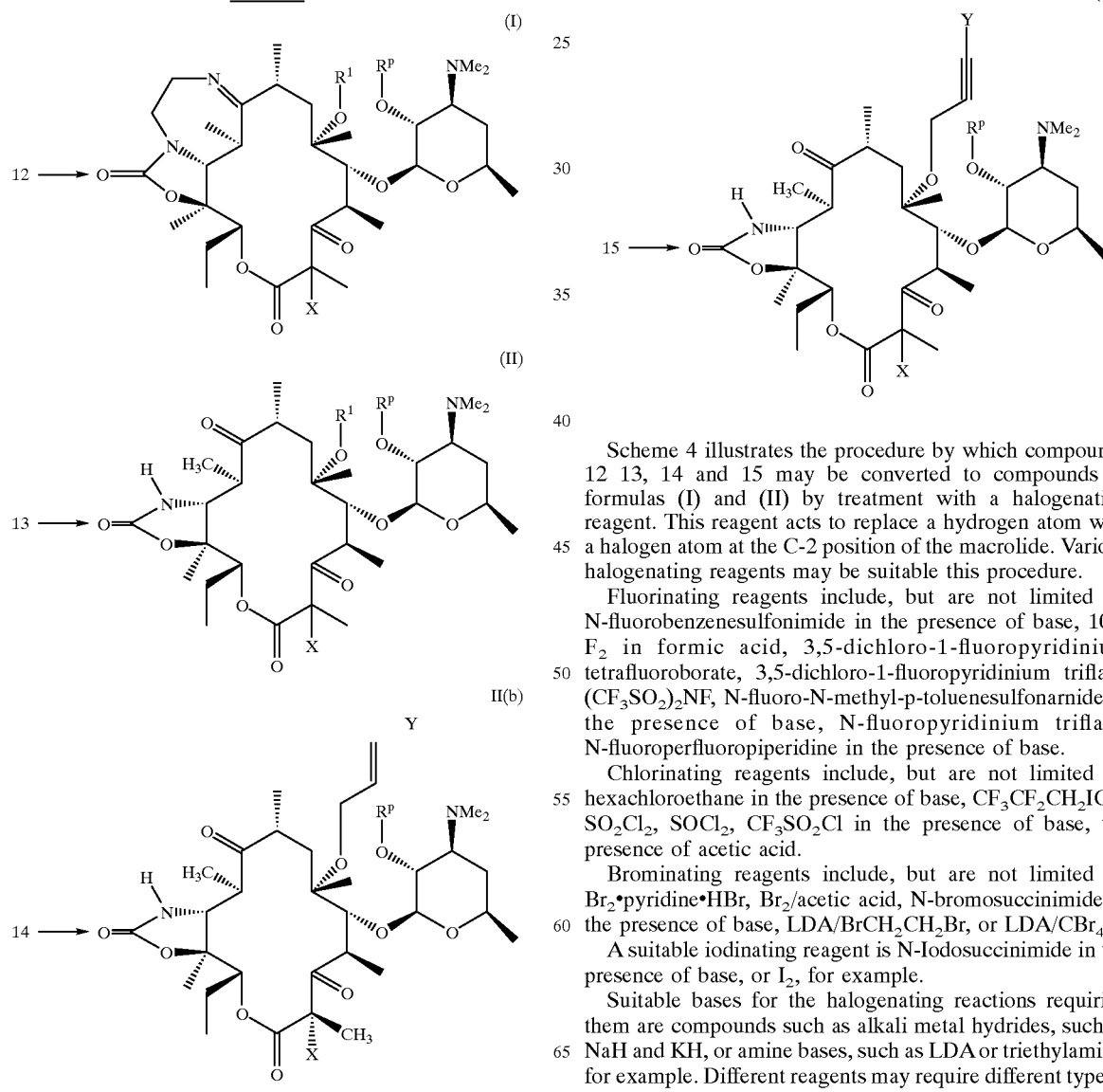

Scheme 4 illustrates the procedure by which compounds 12 13, 14 and 15 may be converted to compounds of formulas (I) and (II) by treatment with a halogenating reagent. This reagent acts to replace a hydrogen atom with a halogen atom at the C-2 position of the macrolide. Various halogenating reagents may be suitable this procedure.

Fluorinating reagents include, but are not limited to, N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base.

Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence of base, the presence of acetic acid.

Brominating reagents include, but are not limited to, $Br_2$•pyridine•HBr, $Br_2$/acetic acid, N-bromosuccinimide in the presence of base, $LDA/BrCH_2CH_2Br$, or $LDA/CBr_4$ A suitable iodinating reagent is N-Iodosuccinimide in the presence of base, or $I_2$, for example.

Suitable bases for the halogenating reactions requiring them are compounds such as alkali metal hydrides, such as NaH and KH, or amine bases, such as LDA or triethylamine, for example. Different reagents may require different type of base, but this is well known within the art.

A preferred halogenating reagent is N-fluorobenzenesulfonimide in the presence of sodium hydride.

The foregoing may be better understood by reference to the following examples which are presented for illustration and not to limit the scope of the inventive concept.

EXAMPLE 1

Compound of Formula (I), $R^P$ is H, $R^1$ is methyl, X is F

Step 1a: Compound of Formula (I), $R^P$ is benzoyl, $R^1$ is methyl, X is F

To a solution of compound 12 of Scheme 3, wherein $R^P$ is benzoyl and $R^1$ is methyl (1.00 g, 1.35 mmol, prepared according to U.S. Pat. No. 5,631,355) in DMF (10 mL) at 0° C. was added NaH (60% in oil, 108 mg, 2.70 mmol), and the mixture was stirred for 30 minutes. To this solution was added N-fluorobenzenesulfonimide (510 mg, 1.62 mmol, Aldrich), and the mixture was stirred at 0° C. for 3 hours. The mixture was taken up in 2-propyl acetate, and the solution was washed with aqueous sodium bicarbonate and brine, dried over sodium sulfate and concentrated under vacuum. Chromatography on silica gel (eluting with 2:1 hexanes:acetone) gave the title compound (615 mg).

Step 1b: Compound of Formula (I), $R^P$ is H, $R^1$ is methyl, X is F

A sample of the compound from Step 1a (600 mg, 0.791 mmol) in methanol (25 mL) was heated at reflux for 24 hours to remove the 2'-benzoyl group. The methanol was removed under vacuum, and the crude product was purified by chromatography on silica gel eluted with 3% methanol in dichlormethane to give the title compound (420 mg).

MS (DCI/NH$_3$) m/z 656 (M+H)$^+$; $^{13}$C NMR (75 MHz, CDCl$_3$) δ d(203.2 and 202.9), 181.1, d(166.2 and 166.0), 155.7, 104.2, d(98.5 and 96.4), 81.4, 80.6, 78.9, 77.9, 70.3, 69.5, 65.8, 60.3, 49.5, 48.5, 42.7, 42.2, 40.5, 40.2, 38.6, 36.1, 28.1, d(25.4 and 25.2), 21.9, 21.1, 19.5, 18.6, 15.1, 12.9, 10.9, 10.4; HRMS m/z calcd (M+H)$^+$ for $C_{33}H_{55}FN_3O_9$: 656.3922. Found: 656.3914.

EXAMPLE 2

Compound of Formula (I), $R^P$ is H, $R^1$ is methyl, X is Cl

To a solution of compound 12 of Scheme 3, wherein $R^P$ is H and $R^1$ is methyl (130 mg, 0.204 mmol, prepared according to U.S. Pat. No. 5,631,355) in N-methylpyrrolidinone (1.5 mL) was added hexachloroethane (50 mg, 0.214 mmol) and sodium carbonate (43 mg, 0.408 mmol). The mixture was stirred for 3 days at room temperature, additional hexachloroethane (50 mg) and sodium carbonate (50 mg) were added and the mixture was stirred at 60° C. for 24 hours. The mixture was taken up in 2-propanol, and the solution was washed with aqueous 5% sodium bicarbonate and brine, dried over sodium sulfate and concentrated under vacuum. Chromatography on silica gel (eluting with acetone) gave the title compound (67 mg).

MS m/z 672 (M+H)$^+$; $^{13}$C NMR (75 MHz, CDCl$_3$) δ 201.3, 181.0, 165.8, 155.9, 104.1, 81.4, 80.7, 79.3, 80.0, 74.2, 70.4, 69.6, 65.9, 60.5, 49.6, 48.4, 42.8, 42.3, 42.2, 40.2, 38.9, 36.2, 31.8, 28.2, 22.1, 21.1, 19.7, 18.7, 16.5, 13.0, 11.0, 10.5; HRMS m/z calcd (M+H)$^+$ for $C_{33}H_{55}ClN_3O_9$: 672.3627. Found: 672.3624.

EXAMPLE 3

Compound of Formula (I), $R^P$ is H, $R^1$ is methyl, X is Br

To a 0° C. solution of compound 12 of Scheme 3, wherein $R^P$ is H and $R^1$ is methyl (500 mg, 0.785 mmol, prepared according to U.S. Pat. No. 5,631,355) in 1:1 dichloromethane/pyridine (4 mL) was added pyridine•HBr$_3$ (352 mg, 1.10 mmol). The mixture was stirred overnight at room temperature, additional pyridine•HBr$_3$ (2 equivalents) was added, and the mixture was stirred at room temperature for 5 hours. The mixture was quenched with aqueous sodium carbonate and saturated aqueous sodium thiosulfate at pH 10. The mixture was extracted with dichloromethane, which was washed with aqueous sodium carbonate and brine, dried over sodium sulfate and concentrated under vacuum. Chromatography on silica gel (eluting with 3–5% (2M NH$_3$ in methanol) in dichloromethane gave the title compound (226 mg).

MS (DCI/NH$_3$) m/z 716 ($^{79}$Br (M+H)$^+$) and 718 ($^{81}$Br (M+H)$^+$); $^{13}$C NMR (75 MHz, CDCl$_3$) δ 201.6, 181.1, 166.1, 155.8, 103.6, 81.4, 80.1, 79.8, 78.8, 70.3, 69.4, 66.0, 65.8, 60.3, 49.4, 48.5, 44.0, 42.8, 42.2, 40.2, 38.8, 36.0, 32.5, 28.2, 20.0, 21.1, 19.6, 18.8, 17.4, 14.0, 13.0, 10.9, 10.4.

EXAMPLE 4

Compound of Formula (II)b, $R^P$ is H, $R^1$ is —CH$_2$—CH=CH—Y, Y is hydrogen, X is F Step 4a: Compound of Formula (II)b, $R^P$ is benzoyl, $R^1$ is —CH$_2$—CH=CH—Y, Y is hydrogen To a solution of compound 14 of Scheme 4, wherein $R^P$ is acetyl and Y is hydrogen (2.00 g, 1 equivalent) in DMF (20 mL) at 0° C. was added NaH (60% in oil, 235 mg, 2 equivalents), and the mixture was stirred at 0° C. for 30 minutes. To this solution was added N-fluorobenzenesulfonimide (1.02 g, 1.1 equivalents), and the mixture was stirred at 0° C. for 3 hours. The mixture was taken up in isopropyl acetate, and the solution was washed sequentially with aqueous NaHCO$_3$ and brine, dried (Na$_2$SO$_4$), filtered, and concentrated. Chromatography of the residue on silica gel with 10–20% acetone in hexanes gave the title compound.

MS (DCI/NH$_3$) m/z 699 (M+H)$^+$; $^{13}$C NMR(75 MHz, CDCl$_3$) δ 217.3, d(203.3 and 203.0), 169.7, d(165.6 and 165.3), 157.4, 135.4, 118.0, 101.5, d(99.3 and 96.6), 83.6, 79.1, 78.7, 78.5, 71.6, 69.2, 64.6, 63.2, 57.6, 44.2, 40.6, 40.5, 38.9, 37.4, 30.6, d(25.1 and 24.9), 22.3, 21.3, 20.9, 20.7, 17.8, 14.9, 13.7, 13.3, 10.6.

Step 4b: Compound of Formula (II)b, $R^P$ is hydrogen, $R^1$ is —CH$_2$—CH=CH—Y, Y is hydrogen A sample of the compound from Step 4a (400 mg, 0.572 mmol) in methanol (10 mL) was stirred at room temperature for 24 hours to remove the 2'-acetyl group. The methanol was removed under vacuum, and the crude product was purified by chromatography on silica gel with 3% methanol in dichloromethane to give 360 mg of the title compound.

$^{13}$C NMR (100 MHz, CDCl$_3$) δ 217.4, d(203.6 and 203.4), d(165.6 and 165.4), 157.4, 135.4, 117.9, 103.9, d(98.7 and 96.7), 83.6, 79.8, 79.1, 78.4, 70.3, 69.6, 65.8, 64.6, 57.5, 44.2, 40.5, 40.2, 38.7, 37.4, 28.2, d(25.3 and 25.1), 22.2, 21.1, 20.7, 17.7, 15.4, 13.8, 13.3, 10.6; HRMS m/z calcd (M+Na)$^+$ for $C_{33}H_{53}N_2O_{10}$FNa: 679.3576. Found: 679.3572.

EXAMPLE 5

Compound of Formula (II)b, $R^P$ is H, $R^1$ is —CH$_2$—CH=CH—Y, Y is 3-quinolyl-, X is F Step 5a: Compound of Formula (II)b, $R^P$ is benzoyl, $R^1$ is —CH$_2$—CH=CH—Y, Y is 3-quinolyl-, X is F To a solution of compound 14 of Scheme 3, wherein $R^P$ is benzoyl and Y is (3-quinolyl) (275 mg, 0.316 mmol, prepared according to U.S. patent application Ser. No.

08/888,350) in DMF (2 mL) at 0° C. was added NaH (60% in oil, 25 mg, 0.632 mmol), and the mixture was stirred at 0° C. for 30 minutes. To this solution was added N-fluorobenzenesulfonimide (119 mg, 0.379 mmol), and the mixture was stirred at 0° C. for 3 hours and at room temperature for 3 hours. The mixture was taken up in propyl acetate, and the solution was washed with aqueous 10% ammonium hydroxide and brine, dried over sodium sulfate and concentrated under vacuum. Chromatography on silica gel (eluting with 10–20% acetone in hexanes) gave the title compound (141 mg). MS m/z 888 (M+H)$^+$.

Step 5b: Compound of Formula (I), R$^P$ is H, R$^1$ is methyl, X is F

A sample of the compound from Step 5a (140 mg, 0.158 mmol) in methanol (30 mL) was heated at reflux for 24 hours to remove the 2'-benzoyl group. The methanol was removed under vacuum, and the crude product was purified by chromatography on silica gel eluted with 3% methanol in dichloromethane to give the title compound (114 mg).

MS (DCI/NH$_3$) m/z 784 (M+H)$^+$; $^{13}$C NMR (75 MHz, CDCl$_3$) δ 217.8, d(204.3 and 203.9), d(165.8 and 165.5), 157.1, 149.6, 147.6, 132.6, 130.1, 129.5, 129.1, 129.0, 128.1, 128.0, 126.7, 104.0, d(99.3 and 96.6), 83.4, 79.5, 79.3, 79.0, 70.3, 69.9, 65.8, 64.2, 58.0, 44.1, 40.7, 40.2, 39.0, 37.4, 28.1, d(25.4 and 25.1) 22.3, 21.1, 20.8, 17.6, 15.4, 13.7, 13.2, 10.6; HRMS m/z calcd (M+H)$^+$ for C$_{42}$H$_{59}$FN$_3$O$_{10}$: 784.4184. Found: 784.4196.

General Experimental Procedure A: Using the Heck Reaction for the Preparation of Compounds of Formula (II)b, Wherein Y is Other than Hydrogen, R$^P$ is Hydrogen, X is F Step a: Compounds of Formula (II)b, Y is other than hydrogen, R$^P$ is —C(O)CH$_3$ or —C(O)C$_6$H$_5$, X is F A mixture comprising a compound of Formula II(b), wherein Y is hydrogen, X is F, and R$^P$ is —C(O)CH$_3$ or —C(O)C$_6$H$_5$ (1 equivalent), Pd(OC(O)CH$_3$)$_2$ (0.2 equivalents), tri-o-tolylphosphine (0.4 equivalents) in acetonitrile was degassed, flushed with nitrogen, treated sequentially with triethylamine (2 equivalents) and aryl halide (2 equivalents), heated at 90° C. for 24 hours, diluted with ethyl acetate, washed sequentially with aqueous NaHCO$_3$ and brine, dried (Na$_2$SO$_4$), filtered, and concentrated. The residue was chromatographed on silica gel to provide the 2'-protected title compound.

Step b: Compounds of Formula (II)b, Y is other than hydrogen, R$^P$ hydrogen, X is F The conversion of compounds of Formula II(b), wherein Y is other than hydrogen, R$^P$ is —C(O)CH$_3$ or —C(O)C$_6$H$_5$, and X is F to compounds of Formula II(b), wherein Y is other than hydrogen, R$^P$ is hydrogen, and X is F was performed by stirring compounds of Formula II(b), wherein Y is other than hydrogen, X is F, and R$^P$ is —C(O)CH$_3$ or —C(O)C$_6$H$_5$ at reflux or at room temperature in methanol overnight to give the title compound after purification by column chromatography on silica gel.

EXAMPLE 6

Compound of Formula (II)b, R$^P$ is H, R$^1$ is —CH$_2$—CH=CH—Y, Y is 6-nitro-3-guinolinyl-, X is F The title compound was prepared from Example 4 (Step 4a) according to Step a and Step b of General Experimental Procedure A.

$^{13}$C NMR(100 MHz, CDCl$_3$) δ 218.0, d(204.4 and 204.1), d(166.0 and 165.8), 157.1, 153.0, 149.3, 145.8, 133.9, 131.4, 131.3, 131.0, 128.9, 127.0, 124.7, 122.4, 104.0, d(99.0 and 96.9), 83.4, 79.5, 79.4, 79.0, 70.3, 69.7, 65.8, 64.0, 58.0, 44.1, 40.8, 40.2, 38.9, 37.4, 28.2, d(25.4 and 25.2), 22.3, 21.1, 20.8, 17.6, 15.4, 13.7, 13.2, 10.7; HRMS m/z calcd (M+H)$^+$ for C$_{42}$H$_{58}$N$_4$O$_{12}$F: 829.4035. Found: 829.4044.

EXAMPLE 7

Compound of Formula (II)b, R$^P$ is H, R$^1$ is —CH$_2$—CH=CH—Y, Y is phenyl-, X is F The title compound was prepared from Example 4 (Step 4a) according to Step a and Step b of General Experimental Procedure A.

MS (DCI/NH$_3$) m/z 733 (M+H)$^+$; $^{13}$C NMR (100 MHz, CDCl$_3$) δ 217.7, d(204.0 and 203.8), d(165.7 and 165.5), 156.9, 136.4, 133.7, 128.7, 127.8, 126.5, 126.1, 104.0, d(98.9 and 96.8), 83.4, 79.7, 79.2, 79.0, 70.3, 69.6, 65.8, 64.2, 58.1, 44.2, 40.6, 40.2, 38.9, 37.4, 28.1, d(25.4 and 25.2), 22.3, 21.1, 20.8, 17.7, 15.4, 13.8, 13.3, 10.8.

EXAMPLE 8

Compound of Formula (II)b, R$^P$ is H, R$^1$ is —CH$_2$—CH=CH—Y, Y is 6-tert butoxycarbonylamino-3-guinolinyl-, X is F The title compound was prepared from Example 4 (Step 4a) according to Step a and Step b of General Experimental Procedure A.

$^{13}$C NMR(100 MHz, CDCl$_3$) δ 217.7, d(204.2 and 203.9), d(165.8 and 165.2), 157.1, 152.6, 148.0, 144.4, 136.7, 132.0, 130.1, 129.9, 129.8, 129.1, 128.6, 122.2, 114.1, 104.0, d(98.9 and 96.9), 83.4, 80.7, 79.6, 79.3, 78.9, 70.3, 69.6, 65.8, 64.3, 58.1, 44.1, 40.7, 40.2, 39.0, 37.4, 28.3, 28.2, d(25.3 and 25.1), 22.3, 21.1, 20.7, 17.6, 15.4, 13.8, 13.2, 10.6; HRMS m/z calcd (M+H)$^+$ for C$_{47}$H$_{68}$N$_4$O$_{10}$F: 899.4812. Found: 899.4816.

EXAMPLE 9

Compound of Formula (II)b, R$^P$ is H, R$^1$ is —CH$_2$—CH=CH—Y, Y is 6-amino-3-quinolinyl-, X is F The title compound was prepared from Example 4 (Step 4a) according to Step a and Step b of General Experimental Procedure A.

$^{13}$C NMR(100 MHz, CDCl$_3$) δ 217.7, d(204.1 and 203.9), d(165.7 and 165.5), 157.1, 145.9, 144.9, 142.7, 130.5, 130.5, 130, 129.6, 129.4, 128.4, 121.2, 107.7, 104.0, d(98.7 and 97.1), 83.4, 79.5, 79.2, 79.0, 70.3, 69.6, 65.7, 64.2, 58.0, 44.1, 40.7, 40.1, 38.9, 37.3, 28.2, d(25.2 and 25.0), 22.2, 21.0, 20.7, 17.5, 15.3, 13.7, 13.1, 10.6.; HRMS m/z calcd (M+H)$^+$ for C$_{42}$H$_{60}$N$_4$O$_{10}$F: 799.4288. Found: 799.4274.

EXAMPLE 10

Compound of Formula (II)b, R$^P$ is H, R$^1$ is —CH$_2$—CH=CH—Y, Y is 6-quinolinyl-, X is F The title compound was prepared from Example 4 (Step 4a) according to Step a and Step b of General Experimental Procedure A.

$^{13}$C NMR(100 MHz, CDCl$_3$) δ 127.8, d(204.2, 203.9), d(165.7 and 165.5), 156.9, 149.9, 148.0, 136.1, 134.7, 132.8, 129.6, 128.4, 127.9, 127.4, 126.1, 121.2, 103.9, d(98.8 and 96.8), 83.3, 79.4, 79.1, 79.0, 70.3, 69.5, 65.7, 64.1, 58.0, 44.1, 40.6, 40.1, 38.9, 37.3, 28.2, d(25.3 and 25.1), 22.2, 21.0, 20.7, 17.5, 15.4, 13.7, 13.2, 10.6; HRMS m/z calcd (M+H)$^+$ for $C_{42}H_{59}N_3O_{10}F$: 784.4184. Found: 784.4172.

EXAMPLE 11

Compound of Formula (II)b, R$^p$ is H, R$^1$ is —CH$_2$—CH=CH—Y, Y is 3-(1,8-naphthyridinyl)-, X is F The title compound was prepared from Example 4 (Step 4a) according to Step a and Step b of General Experimental Procedure A.

$^{13}$C NMR (125 MHz, CDCl$_3$) δ 218.0, d(204.3 and 204.0), d(165.9 and 165.6), 157.2, 152.9, 137.4, 133.3, 131.5, 130.6, 130.4, 129.2, 125.4, 122.7, 122.4, 104.0, d(99.3 and 96.5), 83.5, 79.4,79.4, 78.9, 70.3, 69.6, 65.7, 64.0, 58.0, 44.1, 40.7, 40.2, 38.9, 37.3, 28.2, d(25.4 and 25.1), 22.2, 21.1, 20.8, 17.5, 15.4, 13.7, 13.1, 10.6; HRMS m/z calcd (M+H)$^+$ for $C_{41}H_{58}N_4O_{10}F$: 785.4132. Found: 785.4132.

EXAMPLE 12

Compound of Formula (II)b, R$^p$ is H, R$^1$ is —CH$_2$—CH=CH—Y, Y is 6-quinoxalinyl-, X is F The title compound was prepared from Example 4 (Step 4a) according to Step a and Step b of General Experimental Procedure A.

13C NMR (125 MHz, CDCl$_3$) δ 217.8, d(204.1 and 203.9), d(165.9 and 165.7), 156.9, 145.1, 144.3, 143.4, 142.8, 138.5, 132.0, 129.9, 129.7, 127.8, 127.3, 104.1, d(98.7 and 97.0), 83.3, 79.6, 79.5, 78.9, 70.3, 69.6, 65.8, 64.0, 58.0, 44.2, 40.7, 40.1, 38.9, 37.4, 28.1, d(25.3 and 25.2), 22.3, 21.1, 20.8, 17.6, 15.4, 13.7, 13.2, 10.7; HRMS m/z calcd (M+H)$^+$ for $C_{41}H_{58}N_4O_{10}F$: 785.4131. Found: 785.4133.

EXAMPLE 13

Compound of Formula (II)b, R$^p$ is H, R$^1$ is —CH$_2$—CH=CH—Y, Y is 6-(dimethylamino)-3-quinolinyl-, X is F The title compound was prepared from Example 4 (Step 4a) according to Step a and Step b of General Experimental Procedure A.

$^{13}$C NMR (125 MHz, CDCl$_3$) δ 217.8, d(204.2 and 203.9), d(165.7 and 165.6), 157.2, 148.8, 145.6, 141.9, 130.8, 130.6, 129.6, 129.5, 129.5, 128.2, 119.2, 105.6, 104.0, d(98.8 and 97.1), 83.4, 79.6, 79.3, 79.0, 70.4, 69.6, 65.8, 64.4, 58.1, 44.2, 40.7, 40.7, 40.2, 39.0, 37.4, 28.2, d(25.3, 25.2), 22.3, 21.1, 20.8, 17.6, 15.4, 13.8, 13.2, 10.7; HRMS m/z calcd (M+H)$^+$ for $C_{44}H_{64}N_4O_{10}F$: 827.4601. Found: 827.4605.

EXAMPLE 14

Compound of Formula (II)b, R$^p$ is H, R$^1$ is —CH$_2$—CH=CH—Y, Y is 6-(aminosulfonylmethyl)-3-guinolinyl-, X is F The title compound was prepared from Example 4 (Step 4a) according to Step a and Step b of General Experimental Procedure A.

$^{13}$C NMR (125 MHz, CDCl$_3$) δ 217.6, d(204.3 and 204.1), d(165.8 and 165.6), 157.8, 148.7, 144.9, 135.7, 132.8, 130.7, 130.4, 130.1, 128.8, 128.6, 123.2, 116.1, 104.0, d(98.8 and 97.2), 83.8, 79.3, 79.3, 79.1, 70.4, 69.7, 65.8, 64.2, 58.4, 44.0, 40.8, 40.2, 39.2, 38.9, 37.4, 28.2, d(25.5 and 25.3), 22.4, 21.2, 20.9, 17.6, 15.4, 13.8, 13.3, 10.8; HRMS m/z calcd (M+H)$^+$ for $C_{43}H_{62}N_4O_{12}SF$: 877.4063. Found: 877.4065.

EXAMPLE 15

Compound of Formula (II)b, R$^p$ is H, R$^1$ is —CH$_2$—CH=CH—Y, Y is 6-(aminocarbonyl)-3-quinolinyl-, X is F The title compound was prepared from Example 4 (Step 4a) according to Step a and Step b of General Experimental Procedure A.

$^{13}$C NMR (125 MHz, CDCl$_3$) δ 218.2, d(204.3 and 204.1), 168.9, d(165.5 and 165.3), 157.5, 151.8, 148.8, 132.9, 131.6, 130.5, 129.6, 129.6, 129.6, 128.2, 127.7, 127.1, 104.1, d(98.7 and 97.1), 83.8, 79.5, 79.3, 79.2, 70.4, 69.7, 65.8, 63.8, 58.4, 44.1, 40.7, 40.2, 39.0, 37.4, 28.2, d(25.4 and 25.2), 22.3, 21.1, 21.0, 17.7, 15.5, 13.9, 13.2, 10.6; HRMS m/z calcd (M+H)$^+$ for $C_{43}H_{60}N_4O_{11}F$: 827.4237. Found: 827.4236.

EXAMPLE 16

Compound of Formula (II)b, R$^p$ is H, R$^1$ is —CH$_2$—CH=CH—Y, Y is 6-(N-methylamino)-3-guinolinyl-, X is F The title compound was prepared from Example 4 (Step 4a) according to Step a and Step b of General Experimental Procedure A.

$^{13}$C NMR (125 MHz, CDCl$_3$) δ 127.8, d(204.2 and 204.0), d(165.8 and 165.6), 157.2, 147.4, 145.4, 142.7, 130.6, 130.6, 129.9, 129.8, 129.7, 128.3, 121.0, 104.1, 103.0, d(98.8 and 97.1), 83.5, 79.7, 79.3, 79.0, 70.4, 69.7, 65.9, 64.4, 58.1, 44.2, 40.8, 40.2, 39.0, 37.4, 30.7, 28.2, d(25.3 and 25.2), 22.3, 21.1, 20.9, 17.7, 15.4, 13.8, 13.3, 10.7.; HRMS m/z calcd (M+H)$^+$ for $C_{43}H_{62}N_4O_{10}F$: 813.4445. Found: 813.4436.

EXAMPLE 17

Compound of Formula (II)b, R$^p$ is H, R$^1$ is —CH$_2$—CH=CH—Y, Y is 6-(formyl)-3-guinolinyl-, X is F The title compound was prepared from Example 4 (Step 4a) according to Step a and Step b of General Experimental Procedure A.

$^{13}$C NMR (125 MHz, CDCl$_3$) δ 218.1, d(204.4 and 204.2), 191.6, d(165.9 and 165,7), 157.2, 152.3, 150.1, 134.6, 134.3, 133.7, 130.7, 130.5, 130.4, 129.5, 127.6, 126.1, 104.1, d(98.8 and 97.2), 83.5, 79.5, 79.4, 79.0, 70.4, 69.7, 65.8, 64.1, 58.1, 44.2, 40.8, 40.2, 39.0, 37.4, 28.2, d(25.4 and 25.2), 22.3, 21.2, 20.8, 17.6, 15.4, 13.8, 13.2, 10.7.; HRMS m/z calcd (M+H)$^+$ for $C_{43}H_{59}N_3O_{11}F$: 812.4134. Found: 812.4128.

EXAMPLE 18

Compound of Formula (II)b, R$^p$ is H, R$^1$ is —CH$_2$—CH=CH—Y, Y is 6-[(hydroxyimino)methyl]-3-guinolinyl-, X is F A sample of Example 17 in methanol at room temperature was treated with hydroxyamine hydrochloride, concentrated, and chromatographed on silica gel to provide the title compound.

$^{13}$C NMR (125 MHz, CDCl$_3$) δ 218.0, d(204.4 and 204.1), d(165.9 and 165.7), 157.4, 150.0, 149.2, 148.0, 132.9, 131.3, 130.2, 129.8, 129.6,129.6, 128.1, 128.0, 126.3, 104.0, d(98.8 and 97.2), 83.6, 79.5, 79.4, 79.1, 70.4, 69.6, 65.8, 64.2, 58.2, 44.2, 40.8, 40.2, 39.0, 37.4, 28.3, d(25.4 and 25.2), 22.3, 21.1, 20.8, 17.6, 15.4, 13.8, 13.2, 10.7; HRMS m/z calcd (M+H)$^+$ for C$_{43}$H$_{60}$N$_4$O$_{11}$F: 827.4237. Found: 827.4228.

EXAMPLE 19

Compound of Formula (II)b, R$^P$ is H, R$^1$ is
—CH$_2$—CH═CH—Y, Y is 6-[aminoimino(methyl)]-3-guinolinyl-, X is F A sample of Example 17 in methanol at room temperature was treated with hydrazine, concentrated, and chromatographed on silica gel to provide the tide compound.

$^{13}$C NMR (125 MHz, CDCl$_3$) δ 217.9, d(204.3 and 204.1), d(165.8 and 165.6), 157.2, 149.7, 147.9, 142.2, 133.8, 132.6, 130.0, 130.0, 129.6, 129.3, 128.0, 126.4, 126.2, 104.1, d(98.8, 97.2), 83.5, 79.6, 79.4, 79.0, 70.4, 69.7, 65.8, 64.3, 58.1, 44.2, 40.8, 40.2, 39.0, 37.4, 28.2, d(25.4 and 25.2), 22.3, 21.1, 20.8, 17.6, 15.4, 13.8, 13.2, 10.7; HRMS m/z calcd (M+H)$^+$ for C$_{43}$H$_{61}$N$_5$O$_{10}$F: 826.4397. Found: 826.4395.

EXAMPLE 20

Compound of Formula (II)b, R$^P$ is H, R$^1$ is
—CH$_2$—CH═CH—Y, Y is 6-[[(1-methylethylidene)aminoimino]methyl]-3-guinolinyl-, X is F A sample of Example 19 was treated with acetone at room temperature, concentrated, and chromatographed on silica gel to provide the title compound.

MS (DCI/NH$_3$) m/z 866 (M+H)$^+$; $^{13}$C NMR (125 MHz, CDCl$_3$) δ 217.9, d(204.3 and 204.1), 167.9, d(165.9 and 165.7), 157.1, 156.8, 150.5, 148.8, 133.3, 132.9, 130.2, 129.9, 129.8, 129.7, 129.6, 127.9, 127.1, 104.0, d(98.8 and 97.2), 83.4, 79.5, 79.4, 79.0, 70.4, 69.7, 65.8, 64.3, 58.1, 44.2, 40.8, 40.2, 39.0, 37.4, 28.2, 25.4, d(25.4 and 25.2), 22.3, 21.1, 20.8, 18.7, 17.6, 15.4, 13.8, 13.2, 10.7.

EXAMPLE 21

Compound of Formula (II)b, R$^P$ is H, R$^1$ is
—CH$_2$—CH═CH—Y, Y is 3-(5-cyano)pvridinyl-, X is F The title compound was prepared from Example 4 (Step 4a) according to Step a and Step b of General Experimental Procedure A.

$^{13}$C NMR (125 MHz, CDCl$_3$) δ 218.1, d(204.4 and 204.2), d(166.1 and 165.9), 157.2, 151.2, 150.8, 135.9, 132.6, 132.1, 127.4, 116.5, 110.1, 104.0, d(98.8 and 97.2), 83.4, 79.5, 79.3, 79.0, 70.4, 69.7, 65.8, 63.9, 58.0, 44.1, 40.9, 40.2, 38.9, 37.4, 28.1, d(25.4 and 25.2), 22.3, 21.1, 20.8, 17.6, 15.3, 13.7, 13.2, 10.8; HRMS m/z calcd (M+H)$^+$ for C$_{39}$H$_{56}$N$_4$O$_{10}$F: 759.3579. Found: 759.3573.

EXAMPLE 22

Compound of Formula (II), R$^P$ is hydrogen, R$^1$ is
—CH$_2$—C≡CH—Y, Y is hydrogen, X is F
Step 22a: Compound of Formula (II), R$^P$ is —C(O)CH$_3$, R$^1$ is —CH$_2$—C≡CH—Y, Y is hydrogen, X is F
Compound 15 of Scheme 3, wherein R$^P$ is acetyl and Y is hydrogen, was processed as described in Step 4a to provide the title compound.

MS (DCI/NH$_3$) m/z 697 (M+H)$^+$; $^{13}$C NMR (75 MHz, CDCl$_3$) δ 216.2, d(203.6 and 203.2), 169.7, d(165.8 and 165.5), 157.4, 101.6, d(99.2 and 96.4), 83.5, 80.4, 80.2, 78.8, 78.6, 74.0, 71.6, 69.3, 63.2, 57.6, 50.3, 44.1, 40.6, 40.4, 38.1, 37.4, 30.8, 30.5, d(25.2 and 24.9), 22.2, 21.3, 20.9, 20.1, 17.8, 14.8, 13.7, 13.3, 10.6.

Step 22a: Compound of Formula (II), R$^P$ is hydrogen, R$^1$ is —CH$_2$—C≡CH—Y, Y is hydrogen, X is F The compound described in Step 22a is processed as described in Step 4b to provide the title compound.

General experimental procedure B: using the Sonogashira reaction for the preparation of compounds of Formula II(c), wherein Y is other than hydrogen, R$^P$ is hydrogen, X is F
Step a: Compound of Formula (II), R$^P$ is —C(O)CH$_3$, R$^1$ is —CH$_2$—C≡CH—Y, Y is other than hydrogen, X is F A mixture of a compound of Formula II(c), wherein Y is hydrogen, R$^P$ is —C(O)CH$_3$, and X is F (1 equivalent) and Pd(PPh$_3$)$_2$Cl$_2$ (0.02 equivalents) in 5:1 acetonitrile:triethylamine was degassed and flushed with nitrogen, treated sequentially with CuI (0.01 equivalents) and an aryl halide or arylacyl halide (2–3 equivalents), stirred at room temperature for 10 minutes, heated at 70° C. for 6–24 hours, diluted with ethyl acetate or isopropyl acetate, washed sequentially with water and brine, dried (Na$_2$SO$_4$), and chromatographed on silica gel gave the 2'-protected protected compound Formula II(c), wherein Y is other than hydrogen H and R$^P$—C(O)CH$_3$.

Step b: Compound of Formula (II), R$^P$ is hydrogen, R$^1$ is —CH$_2$—C≡CH—Y, Y is other than hydrogen, X is F The conversion of compounds of Formula II(c), wherein Y is other than hydrogen, R$^P$ is —C(O)CH$_3$, and X is F to compounds of Formula II(c), wherein Y is other than hydrogen, R$^P$ is hydrogen, and X is F was performed by stirring compounds of Formula II(c), wherein Y is other than hydrogen, X is F, and R$^P$ is —C(O)CH$_3$ at reflux or at room temperature in methanol overnight to give the title compound after purification by column chromatography on silica gel.

EXAMPLE 23

Compound of Formula (II), R$^P$ is hydrogen, R$^1$ is
—CH$_2$—C≡CH—Y, Y is phenylcarbonyl-, X is F The title compound was prepared from Example 22 (Step 22a) according to Step a and Step b of General Experimental Procedure B.

$^{13}$C NMR (75 MHz, CDCl$_3$) δ 215.9, d(204.3, 203.9), 177.8, d(166.2, 166.9), 157.5, 136.4, 134.1, 129.9, 128.5, 104.1, d(98.9 and 96.1), 91.3, 84.1, 83.2, 80.8, 80.7, 78.9, 70.2, 69.5, 65.8, 58.2, 50.3, 44.0, 40.3, 40.1, 38.2, 37.7, 31.5, d(25.5 and 25.2), 22.2, 21.2, 20.3, 17.7, 15.5, 14.1, 13.8, 13.3, 10.5; HRMS m/z calcd (M+H)$^+$ for C$_{40}$H$_{56}$N$_2$O$_{11}$F: 759.3868. Found: 759.3888.

EXAMPLE 24

Compound of Formula (II), R$^P$ is hydrogen, R$^1$ is
—CH$_2$—C≡CH—Y, Y is 2-thienylcarbonyl-, X is F The title compound was prepared from Example 22 (Step 22a) according to Step a and Step b of General Experimental Procedure B.

$^{13}$C NMR (125 MHz, CDCl$_3$) δ 216.1, d(204.3 and 203.9), 169.5, d(166.2 and 166.9), 157.4, 144.4, 135.8, 135.4, 128.2, 104.2, d(98.9 and 96.1), 89.6, 83.5, 83.2, 80.9, 80.6, 78.9, 70.3, 69.8, 65.8, 58.2, 50.3, 44.0, 40.3, 40.2, 38.2, 37.7, 28.2, d(25.5 and 25.2), 22.2, 21.2, m 20.3, 17.7, 15.5, 13.8, 13.3, 10.5; HRMS m/z calcd (M+H)+ for $C_{38}H_{54}N_2O_{11}FS$: 765.3427. Found: 765.3429.

EXAMPLE 25

Compound of Formula (II), $R^p$ is hydrogen, $R^1$ is —$CH_2$—C≡CH—Y, Y is (6-chloro-3-pyridinyl)carbonyl-, X is F The title compound was prepared from Example 22 (Step 22a) according to Step a and Step b of General Experimental Procedure B.

MS (DCI/NH$_3$) m/z 794 (M+H)+; $^{13}$C NMR (125 MHz, CDCl$_3$) δ partial 217.7, d(203.3 and 202.9), d(172.8 and 172.5), 157.4, 144.5, 132.8, 124.1, 104.8, d(92.2 and 87.6).

EXAMPLE 26

Compound of Formula (II), $R^p$ is hydrogen, $R^1$ is —$CH_2$—C≡CH—Y, Y is 3-quinolinyl-, X is F The title compound was prepared from Example 22 (Step 22a) according to Step a and Step b of General Experimental Procedure B.

$^{13}$C NMR (125 MHz, CDCl$_3$) δ 216.7, d(204.1 and 203.8), d(166.0 and 165.8), 157.3, 152.3, 146.9, 138.5, 129.9, 129.2, 127.8, 127.3, 127.0, 117.1, 104.1, d(98.5 and 96.8), 89.4, 83.5, 82.9, 80.3, 80.0, 78.6, 70.3, 69.7, 65.8, 58.0, 51.1, 44.2, 40.6, 40.2, 38.5, 37.4, 29.2, 28.1, d(25.2 and 25.0), 22.2, 21.1, 20.2, 17.6, 15.4, 13.7, 13.2, 10.6. Anal. calcd for $C_{42}H_{56}FN_3O_{10}$: C, 64.52, H, 7.22, N, 5.37. Found: C, 64.26, H, 7.37, N 5.04; HRMS m/z calcd (M+H)+ for $C_{42}H_{57}N_3O_{10}FS$: 782.4028. Found: 782.4003.

EXAMPLE 27

Compound of Formula (II), $R^p$ is hydrogen, $R^1$ is —$CH_2$—C≡CH—Y, Y is 8-sulfonylamino-3-quinolinyl-, X is F The title compound was prepared from Example 22 (Step 22a) according to Step a and Step b of General Experimental Procedure B.

$^{13}$C NMR (125 MHz, CDCl$_3$) δ 216.9, d(204.2 and 203.9), d(166.0 and 165.8), 157.4, 153.3, 141.6, 139.1, 138.6, 132.9, 129.3, 127.9, 126.2, 118.5, 104.1, d(98.5 and 96.8), 91.1, 83.6, 81.9, 80.4, 79.8, 78.6, 70.3, 69.7, 65.7, 58.0, 51.0, 44.2, 40.6, 40.1, 38.3, 37.4, 28.1, d(25.3 and 25.1), 22.2, 21.1, 20.3, 17.6, 15.3, 13.7, 13.2, 10.6; HRMS m/z calcd (M+H)+ for $C_{42}H_{58}N_4O_{12}FS$: 861.3756. Found: 861.3751.

EXAMPLE 28

Compound of Formula (II), $R^p$ is hydrogen, $R^1$ is —$CH_2$—C≡CH—Y, Y is (2,2'-bisthien)-5-yl-, X is F The title compound was prepared from Example 22 (Step 22a) according to Step a and Step b of General Experimental Procedure B.

$^{13}$C NMR (125 MHz, CDCl$_3$) δ 216.6, d(204.1 and 203.8), d(165.8 and 165.6), 157.2, 138.9, 136.8, 133.3, 127.8, 124.7, 124.3, 123.5, 121.5, 104.1, d(98.4 and 96.8), 90.8, 83.5, 80.1, 79.0, 78.8, 70.3, 69.7, 65.8, 58.1, 51.2, 44.2, 40.5, 40.2, 38.4, 37.4, 28.2, d(25.3 and 25.2), 22.3, 21.1, 20.3, 17.7, 15.4, 13.8, 13.3, 10; HRMS m/z calcd (M+H)+ for $C_{41}H_{56}N_2O_{10}FS_2$: 819.3360. Found: 819.3353.

EXAMPLE 29

Compound of Formula (II), $R^p$ is hydrogen, $R^1$ is —$CH_2$—C≡CH—Y, Y is [5-(2-pyridyl)-2-thienyl]-, X is F The title compound was prepared from Example 22 (Step 22a) according to Step a and Step b of General Experimental Procedure B.

$^{13}$C NMR (125 MHz, CDCl$_3$) δ 216.3, d(203.9 and 203.7), d(165.8 and 165.6), 157.2, 152.0, 149.5, 145.9, 136.5, 133.3, 124.5, 124.4, 122.0, 118.9, 104.1, d(98.4 and 96.8), 91.2, 83.4, 80.1, 80.1, 79.3, 78.7, 70.3, 69.6, 65.8, 58.1, 51.1, 44.1, 40.4, 40.1, 38.3, 37.4, 28.2, d(25.3 and 25.1), 22.2, 21.1, 20.2, 17.6, 15.3, 13.7, 13.2, 10.6.

Examples 30 through 97 may be prepared according to the procedures described in Examples 1 through 29 and the synthetic schemes and discussions contained herein.

EXAMPLE 30

Compound of Formula (II)b, $R^p$ is H, $R^1$ is —$CH_2$—CH=CH—Y, Y is 5-(3-pyridinyl)-2-pyrrolyl-, X is F

EXAMPLE 31

Compound of Formula (II)b, $R^p$ is H, $R^1$ is —$CH_2$—CH=CH—Y, Y is 5-(2-pyrazinyl)-2-pyrrolyl-, X is F

EXAMPLE 32

Compound of Formula (II)b, $R^p$ is H, $R^1$ is —$CH_2$—CH=CH—Y, Y is 5-(4-pyridinyl)-2-pyrrolyl-, X is F

EXAMPLE 33

Compound of Formula (II)b, $R^p$ is H, $R^1$ is —$CH_2$—CH=CH—Y, Y is 5-(2-pyridinyl)-2-pyrrolyl-, X is F

EXAMPLE 34

Compound of Formula (II)b, $R^p$ is H, $R^1$ is —$CH_2$—CH=CH—Y, Y is 2-quinoxalinyl-, X is F

EXAMPLE 35

Compound of Formula (II)b, $R^p$ is H, $R^1$ is —$CH_2$—CH=CH—Y, Y is 5-(1-methyl-2-pyridinyl)-2-pyrrolyl-, X is F

EXAMPLE 36

Compound of Formula (II)b, $R^p$ is H, $R^1$ is —$CH_2$—CH=CH—Y, Y is 5-(1-methyl-2-pyrazinyl)-2-pyrrolyl-, X is F

EXAMPLE 37

Compound of Formula (II)b, $R^p$ is H, $R^1$ is —$CH_2$—CH=CH—Y, Y is 5-(2-pyrazinyl)-2-furanyl-, X is F

EXAMPLE 38

Compound of Formula (II)b, $R^p$ is H, $R^1$ is —$CH_2$—CH=CH—Y, Y is 5-(3-pyridinyl)-2-furanyl-, X is F

EXAMPLE 39

Compound of Formula (II)b, $R^p$ is H, $R^1$ is —$CH_2$—CH=CH—Y, Y is 5-(2-pyridinyl)-2-furanyl-, X is F

EXAMPLE 40

Compound of Formula (II)b, $R^p$ is H, $R^1$ is —CH$_2$—CH=CH—Y, Y is 7-[(methoxyimino)methyl]-7-quinoxalinyl-, X is F

EXAMPLE 41

Compound of Formula (II)b, $R^p$ is H, $R^1$ is —CH$_2$—CH=CH—Y, Y is 5-(3-pyridinyl)-2-thienyl-, X is F

EXAMPLE 42

Compound of Formula (II)b, $R^p$ is H, $R^1$ is —CH$_2$—CH=CH—Y, Y is 5-(2-pyrazinyl)-2-thienyl-, X is F

EXAMPLE 43

Compound of Formula (II)b, $R^p$ is H, $R^1$ is —CH$_2$—CH=CH—Y, Y is 5-(4-pyridinyl)-2-thienyl]

EXAMPLE 44

Compound of Formula (II)b, $R^p$ is H, $R^1$ is —CH$_2$—CH=CH—Y, Y is 5-[5-(aminocarbonyl)-3-pyridinyl]-2-thienyl-, X is F

EXAMPLE 45

Compound of Formula (II)b, $R^p$ is H, $R^1$ is —CH$_2$—CH=CH—Y, Y is 5-(2-thiazoyl)-2-thienyl-, X is F

EXAMPLE 46

Compound of Formula (II)b, $R^p$ is H, $R^1$ is —CH$_2$—CH=CH—Y, Y is 5-(5-thiazoyl)-2-thienyl-, X is F

EXAMPLE 47

Compound of Formula (II)b, $R^p$ is H, $R^1$ is —CH$_2$—CH=CH—Y, Y is 5-[2-(methyl)-5-thiazoyl]-2-thienyl-, X is F

EXAMPLE 48

Compound of Formula (II)b, $R^p$ is H, $R^1$ is —CH$_2$—CH=CH—Y, Y is 7-[(hydroxyimino)methyl]-7-guinoxalinyl-, X is F

EXAMPLE 49

Compound of Formula (II)b, $R^p$ is H, $R^1$ is —CH$_2$—CH=CH—Y, Y is 5-(5-pyrimidinyl)-2-thienyl-, X is F

EXAMPLE 50

Compound of Formula (II)b, $R^p$ is H, $R^1$ is —CH$_2$—CH=CH—Y, Y is 5-(2-pyrmidinyl)-2-thienyl-, X is F

EXAMPLE 51

Compound of Formula (II)b, $R^p$ is H, $R^1$ is —CH$_2$—CH=CH—Y, Y is 5-[5-(methoxycarbonyl)-3-pyridinyl]-2-thienyl-, X is F

EXAMPLE 52

Compound of Formula (II)b, $R^p$ is H, $R^1$ is —CH$_2$—CH=CH—Y, Y is 5-thieno[2,3-b]pyridinyl-, X is F

EXAMPLE 53

Compound of Formula (II)b, $R^p$ is H, $R^1$ is —CH$_2$—CH=CH—Y, Y is 1H-pyrrolo[2,3-b]pyndinyl-, X is F

EXAMPLE 54

Compound of Formula (II)b, $R^p$ is H, $R^1$ is —CH$_2$—CH=CH—Y, Y is 3H-3-methylimidazo[4,5-b]pyridinyl-, X is F

EXAMPLE 55

Compound of Formula (II)b, $R^p$ is H, $R^1$ is —CH$_2$—CH=CH—Y, Y is 6-carboxy-3-quinolinyl-, X is F

EXAMPLE 56

Compound of Formula (II)b, $R^p$ is H, $R^1$ is —CH$_2$—CH=CH—Y, Y is 5-(2-thienyl)-2-thiazoyl-, X is F

EXAMPLE 57

Compound of Formula (II)b, $R^p$ is H, $R^1$ is —CH$_2$—CH=CH—Y, Y is 2-(2-thienyl)-5-thiazoyl-, X is F

EXAMPLE 58

Compound of Formula (II)b, $R^p$ is H, $R^1$ is —CH$_2$—CH=CH—Y, Y is 2-(3-pyridyl)-5-thiazoyl-, X is F

EXAMPLE 59

Compound of Formula (II)b, $R^p$ is H, $R^1$ is —CH$_2$—CH=CH—Y, Y is 5-(3-pyridyl)-2-thiazoyl-, X is F

EXAMPLE 60

Compound of Formula (II)b, $R^p$ is H, $R^1$ is —CH$_2$—CH=CH—Y, Y is 5-(2-pyrazinyl)-3-pyridinyl-, X is F

EXAMPLE 61

Compound of Formula (II)b, $R^p$ is H, $R^1$ is —CH$_2$—CH=CH—Y, Y is 5-[(2-pyridinylamino)carbonyl]-3-pyridinyl-, X is F

EXAMPLE 62

Compound of Formula (II)b, $R^p$ is H, $R^1$ is —CH$_2$—CH=CH—Y, Y is 5-[(3-pyridinylamino)carbonyl]-3-pyridinyl-, X is F

EXAMPLE 63

Compound of Formula (II)b, $R^p$ is H, $R^1$ is —CH$_2$—CH=CH—Y, Y is 5-[[(4-chlorophenyl)amino]carbonyl]-3-pyridinyl-, X is F

EXAMPLE 64

Compound of Formula (II)c, $R^p$ is H, $R^1$ is —CH$_2$—C≡CH—Y, Y is 5-(3-pyridinyl)-2-pyrrolyl-, X is F

EXAMPLE 65

Compound of Formula (II)c, $R^p$ is H, $R^1$ is —CH$_2$—C≡CH—Y, Y is 5-(2-pyrazinyl)-2-pyrrolyl-, X is F

EXAMPLE 66
Compound of Formula (II)c, $R^p$ is H, $R^1$ is —CH$_2$—C≡CH—Y, Y is 5-(4-pyridinyl)-2-pyrrolyl-, X is F

EXAMPLE 67
Compound of Formula (II)c, $R^p$ is H, $R^1$ is —CH$_2$—C≡CH—Y, Y is 5-(2-pyridinyl)-2-pyrrolyl-, X is F

EXAMPLE 68
Compound of Formula (II)c, $R^p$ is H, $R^1$ is —CH$_2$—C≡CH—Y, Y is 2-quinoxalinyl-, X is F

EXAMPLE 69
Compound of Formula (II)c, $R^p$ is H, $R^1$ is —CH$_2$—C≡CH—Y, Y is 5-(1-methyl-2-pyridinyl)-2-pyrrolyl-, X is F

EXAMPLE 70
Compound of Formula (II)c, $R^p$ is H, $R^1$ is —CH$_2$—C≡CH—Y, Y is 5-(1-methyl-2-pyrazinyl)-2-pyrrolyl-, X is F

EXAMPLE 71
Compound of Formula (II)c, $R^p$ is H, $R^1$ is —CH$_2$—C≡CH—Y, Y is 5-(2-pyrazinyl)-2-furanyl-, X is F

EXAMPLE 72
Compound of Formula (II)c, $R^p$ is H, $R^1$ is —CH$_2$—C≡CH—Y, Y is 5-(3-pyridinyl)-2-furanyl-, X is F

EXAMPLE 73
Compound of Formula (II)c, $R^p$ is H, $R^1$ is —CH$_2$—C≡CH—Y, Y is 5-(2-pyridinyl)-2-furanyl-, X is F

EXAMPLE 74
Compound of Formula (II)c, $R^p$ is H, $R^1$ is —CH$_2$—C≡CH—Y Y is 7-[(methoxyimino)methyl]-7-quinoxalinyl-, X is F

EXAMPLE 75
Compound of Formula (II)c, $R^p$ is H, $R^1$ is —CH$_2$—C≡CH—Y, Y is 5-(3-pyridinyl)-2-thienyl-, X is F

EXAMPLE 76
Compound of Formula (II)c, $R^p$ is H, $R^1$ is —CH$_2$—C≡CH—Y, Y is 5-(2-pyrazinyl)-2-thienyl-, X is F

EXAMPLE 77
Compound of Formula (II)c, $R^p$ is H, $R^1$ is —CH$_2$—C≡CH—Y, Y is 5-(4-pyridinyl)-2-thienyl]

EXAMPLE 78
Compound of Formula (II)c, $R^p$ is H, $R^1$ is —CH$_2$—C≡CH—Y, Y is 5-[5-(aminocarbonyl)-3-pyridinyl]-2-thienyl-, X is F

EXAMPLE 79
Compound of Formula (II)c, $R^p$ is H, $R^1$ is —CH$_2$—C≡CH—Y, Y is 5-(2-thiazoyl)-2-thienyl-, X is F

EXAMPLE 80
Compound of Formula (II)c, $R^p$ is H, $R^1$ is —CH$_2$—C≡CH—Y, Y is 5-(5-thiazoyl)-2-thienyl-, X is F

EXAMPLE 81
Compound of Formula (II)c, $R^p$ is H, $R^1$ is —CH$_2$—C≡CH—Y, Y is 5-[2-(methyl)-5-thiazoyl]-2-thienyl-, X is F

EXAMPLE 82
Compound of Formula (II)c, $R^p$ is H, $R^1$ is —CH$_2$—C≡CH—Y, Y is 7-[(hydroxyimino)methyl]-7-quinoxalinyl-, X is F

EXAMPLE 83
Compound of Formula (II)c, $R^p$ is H, $R^1$ is —CH$_2$—C≡CH—Y, Y is 5-(5-pyrimidinyl)-2-thienyl-, X is F

EXAMPLE 84
Compound of Formula (II)c, $R^p$ is H, $R^1$ is —CH$_2$—C≡CH—Y, Y is 5-(2-pyrimidinyl)-2-thienyl-, X is F

EXAMPLE 85
Compound of Formula (II)c, $R^p$ is H, $R^1$ is —CH$_2$—C≡CH—Y, Y is 5-[5-(methoxycarbonyl)-3-pyridinyl)-2-thienyl-, X is F

EXAMPLE 86
Compound of Formula (II)c, $R^p$ is H, $R^1$ is —CH$_2$—C≡CH—Y, Y is 5-thieno[2,3-b]pyridinyl-, X is F

EXAMPLE 87
Compound of Formula (II)c, $R^p$ is H, $R^1$ is —CH$_2$—C≡CH—Y, Y is 1H-pyrrolo[2,3-b]pyridinyl-, X is F

EXAMPLE 88
Compound of Formula (II)c, $R^p$ is H, $R^1$ is —CH$_2$—C≡CH—Y, Y is 3H-3-methylimidazo[4,5-b]pyridinyl-, X is F

EXAMPLE 89
Compound of Formula (II)c, $R^p$ is H, $R^1$ is —CH$_2$—C≡CH—Y, Y is 6-carboxy-3-quinolinyl-, X is F

EXAMPLE 90
Compound of Formula (II)c, $R^p$ is H, $R^1$ is —CH$_2$—C≡CH—Y, Y is 5-(2-thienyl)-2-thiazoyl-, X is F

EXAMPLE 91
Compound of Formula (II)c, $R^p$ is H, $R^1$ is —CH$_2$—C≡CH—Y, Y is 2-(2-thienyl)-5-thiazoyl-, X is F

EXAMPLE 92
Compound of Formula (II)c, $R^p$ is H, $R^1$ is —CH$_2$—C≡CH—Y, Y is 2-(3-pyridyl)-5-thiazoyl-, X is F

EXAMPLE 93
Compound of Formula (II)c, $R^p$ is H, $R^1$ is —CH$_2$—C≡CH—Y, Y is 5-(3-pyridyl)-2-thiazoyl-, X is F

EXAMPLE 94
Compound of Formula (II)c, $R^p$ is H, $R^1$ is —CH$_2$—C≡CH—Y, Y is 5-(2-pyrazinyl)-3-pyridinyl-, X is F

EXAMPLE 95
Compound of Formula (II)c, $R^p$ is H, $R^1$ is —CH$_2$—C≡CH—Y, Y is 5-[(2-pyridinylamino)carbonyl]-3-pyridinyl-, X is F

EXAMPLE 96
Compound of Formula (II)c, $R^p$ is H, $R^1$ is —CH$_2$—C≡CH—Y, Y is 5-[(3-pyridinylamino)carbonyl]-3-pyridinyl-, X is F

EXAMPLE 97
Compound of Formula (II)c, $R^p$ is H, $R^1$ is —CH$_2$—C≡CH—Y, Y is 5-[[(4-chlorophenyl)amino]carbonyl]-3-pyridinyl-, X is F

What is claimed is:
1. A compound selected from the group consisting of:

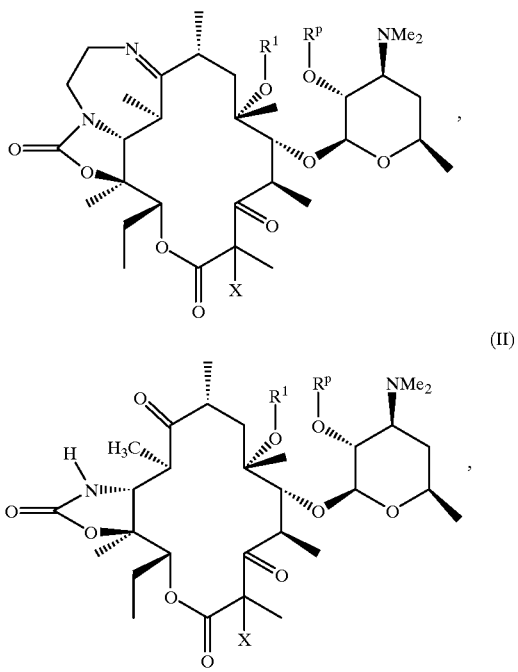

and pharmaceutically acceptable salts and esters thereof, wherein
$R^p$ is hydrogen or a hydroxy protecting group;
X is F; and
$R^1$ is selected from the group consisting of
(1) $C_1$–$C_6$-alkyl optionally substituted with one or more substituents selected from the group consisting of
 (a) aryl,
 (b) substituted aryl,
 (c) heteroaryl,
 (d) substituted heteroaryl,
 (e) —$NR^3R^4$ wherein $R^3$ and $R^4$ are independently selected from hydrogen and $C_1$–$C_3$-alkyl, or $R^3$ and $R^4$ are taken together with the atom to which they are attached form a 3–7 membered ring containing a moiety selected from the group consisting of —O—, —NH—, —N($C_1$–$C_6$-alkyl-)-, —N (aryl-$C_1$–$C_6$-alkyl-)-, —N(substituted aryl-$C_1$–$C_6$-alkyl-)-, —N (heteroaryl-$C_1$–$C_6$-alkyl-)-, and —N(substituted heteroaryl-$C_1$–$C_6$-alkyl-)-;
(2) —$CH_2$—CH═CH—Y, wherein Y is selected from the group consisting of
 (a) H,
 (b) aryl,
 (c) substituted aryl,
 (d) heteroaryl,
 (e) substituted heteroaryl;
 (f) —CH═$CH_2$,
 (g) —CH═CH-aryl,
 (h) —CH═CH-substituted aryl,
 (i) —CH═CH-heteroaryl, and
 (j) —CH═CH-substituted heteroaryl,
 (k) (aryl)oyl,
 (l) (substituted aryl)oyl,
 (m) (heteroaryl)oyl, and
 (n) (substituted heteroaryl)oyl; and (3) —$CH_2$—C≡C—Y, wherein Y is as defined previously,
with the proviso that in compounds of formula (II) wherein $R^1$ is selected from option (1) the $C_1$–$C_6$-alkyl group must be substituted.

2. A compound according to claim 1 which is selected from the group consisting of:

Compound of Formula (I), $R^p$ is H, $R^1$ is methyl, X is F;
Compound of Formula (II)b, $R^p$ is H, $R^1$ is —$CH_2$—CH═CH—Y, Y is hydrogen, X is F;
Compound of Formula (II)b, $R^p$ is H, $R^1$ is —$CH_2$—CH═CH—Y, Y is (3-quinolyl), X is F;
Compound of Formula (II)b, $R^p$ is H, $R^1$ is —$CH_2$—CH═CH—Y, Y is 6-nitro-3-quinolinyl-, X is F;
Compound of Formula (II)b, $R^p$ is H, $R^1$ is —$CH_2$—CH═CH—Y, Y is phenyl-, X is F;
Compound of Formula (II)b, $R^p$ is H, $R^1$ is —$CH_2$—CH═CH—Y, Y is 6-tert butoxycarbonylamino-3-quinolinyl-, X is F;
Compound of Formula (II)b, $R^p$ is H, $R^1$ is —$CH_2$—CH═CH—Y, Y is 6-amino-3-quinolinyl-, X is F;
Compound of Formula (II)b, $R^p$ is H, $R^1$ is —$CH_2$—CH═CH—Y, Y is 6-quinolinyl-, X is F;
Compound of Formula (II)b, $R^p$ is H, $R^1$ is —$CH_2$—CH═CH—Y, Y is 3-(1,8-naphthyridinyl)-, X is F;
Compound of Formula (II)b, $R^p$ is H, $R^1$ is —$CH_2$—CH═CH—Y, Y is 6-quinoxalinyl-, X is F;
Compound of Formula (II)b, $R^p$ is H, $R^1$ is —$CH_2$—CH═CH—Y, Y is 6-(dimethylamino)-3-quinolinyl-, X is F;
Compound of Formula (II)b, $R^p$ is H, $R^1$ is —$CH_2$—CH═CH—Y, Y is 6-(aminosulfonylmethyl)-3-quinolinyl-, X is F;
Compound of Formula (II)b, $R^p$ is H, $R^1$ is —$CH_2$—CH═CH—Y, Y is 6-(aminocarbonyl)-3-quinolinyl-, X is F;
Compound of Formula (II)b, $R^p$ is H, $R^1$ is —$CH_2$—CH═CH—Y, Y is 6-(N-methylamino)-3-quinolinyl-, X is F;
Compound of Formula (II)b, $R^p$ is H, $R^1$ is —$CH_2$—CH═CH—Y, Y is 6-(formyl)-3-quinolinyl-, X is F;
Compound of Formula (II)b, $R^p$ is H, $R^1$ is —$CH_2$—CH═CH—Y, is 6-[(hydroxyimino)methyl]-3-quinolinyl-, X is F;
Compound of Formula (II)b, $R^p$ is H, $R^1$ is —$CH_2$—CH═CH—Y, Y is 6-[aminoimino(methyl)]-3-quinolinyl-, X is F;
Compound of Formula (II)b, $R^p$ is H, $R^1$ is —$CH_2$—CH═CH—Y, Y is 6-[[(1-methylethylidene)aminoimino]methyl]-3-quinolinyl-, X is F;
Compound of Formula (II)b, $R^p$ is H, $R^1$ is —$CH_2$—CH═CH—Y, Y is 3-(5-cyano)pyridinyl-, X is F;
Compound of Formula (II), $R^p$ is hydrogen, $R^1$ is —$CH_2$—C≡C—Y, Y is hydrogen, X is F;
Compound of Formula (II), $R^p$ is hydrogen, $R^1$ is —$CH_2$—C≡C—Y, Y is phenylcarbonyl-, X is F;
Compound of Formula (II), $R^p$ is hydrogen, $R^1$ is —$CH_2$—C≡C—Y, Y is 2-thienylcarbonyl-, X is F;
Compound of Formula (II), $R^p$ is hydrogen, $R^1$ is —$CH_2$—C≡C—Y, Y is (6-chloro-3-pyridinyl)carbonyl-, X is F;
Compound of Formula (II), $R^p$ is hydrogen, $R^1$ is —$CH_2$—C≡C—Y, Y is 3-quinolinyl-, X is F;

Compound of Formula (II), $R^P$ is hydrogen, $R^1$ is —$CH_2$—C≡C—Y, Y is 8-sulfonylamino-3-quinolinyl-, X is F;

Compound of Formula (II), $R^P$ is hydrogen, $R^1$ is —$CH_2$—C≡C—Y, Y is (2,2'-bisthien)-5-yl-, X is F; and Compound of Formula (II), $R^P$ is hydrogen, $R^1$ is —$CH_2$—C≡C—Y, Y is [5-(2-pyridyl)-2-thienyl]-, X is F.

3. A pharmaceutical composition for treating bacterial infections comprising a therapeutically effective amount of a compound of claim 1 or a pharmaceutically acceptable salt or ester thereof in combination with a pharmaceutically acceptable carrier.

4. A method for treating bacterial infections comprising administering to a mammal in need of such treatment a pharmaceutical composition containing a therapeutically-effective amount of a compound of claim 1 or a pharmaceutically acceptable salt or ester thereof.

5. A compound according to claim 1 having the formula (I)

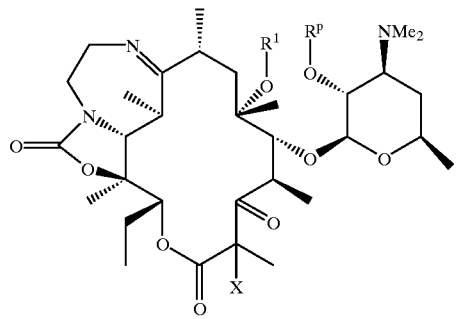

6. A compound according to claim 5 wherein X is F.

7. A compound according to claim 1 having the formula (II)

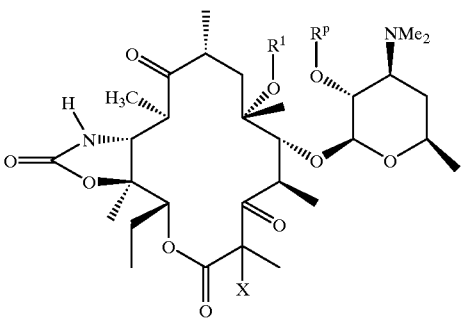

8. A compound according to claim 7 wherein X is F.

9. A compound according to claim 1 having the formula (II)b

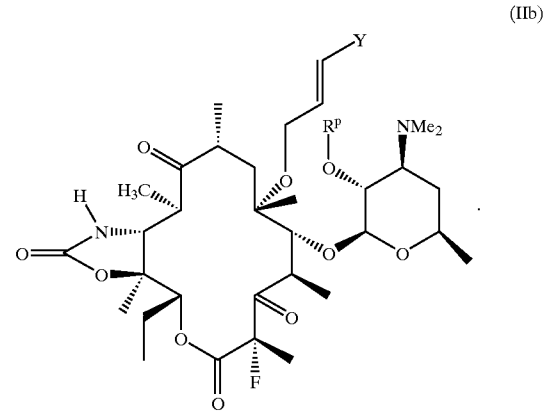

10. A process for preparing a compound having the formula

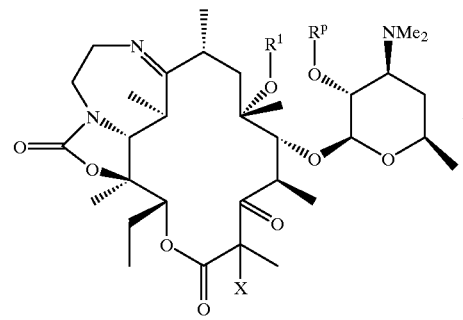

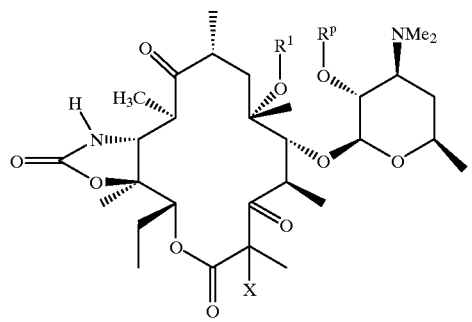

wherein
$R^P$ is hydrogen or a hydroxy protecting group;
X is F, Cl, Br, or I; and
$R^1$ is selected from the group consisting of
(1) $C_1$–$C_6$-alkyl optionally substituted with one or more substituents selected from the group consisting of
(a) aryl,
(b) substituted aryl,
(c) heteroaryl,
(d) substituted heteroaryl,
(e) —$NR^3R^4$ wherein $R^3$ and $R^4$ are independently selected from hydrogen and $C_1$–$C_3$-alkyl, or $R^3$ and $R^4$ are taken together with the atom to which they are attached form a 3–7 membered ring containing a moiety selected from the group consisting of —O—, —NH—, —N($C_1$–$C_6$-alkyl-)-, —N (aryl-$C_1$–$C_6$-alkyl-)-, —N(substituted aryl-$C_1$–$C_6$-alkyl-)-, —N (heteroaryl-$C_1$–$C_6$-alkyl-)-, and —N(substituted heteroaryl-$C_1$–$C_6$-alkyl-)-;

(2) —$CH_2$—CH═CH—Y, wherein Y is selected from the group consisting of
(a) H,
(b) aryl,
(c) substituted aryl,
(d) heteroaryl,
(e) substituted heteroaryl;
(f) —CH═$H_2$,
(g) —CH═CH-aryl,
(h) —CH═CH-substituted aryl,
(i) —CH═CH-heteroaryl, and
(j) —CH═CH-substituted heteroaryl,
(k) (aryl)oyl,
(l) (substituted aryl)oyl,
(m) (heteroaryl)oyl, and
(n) (substituted heteroaryl)oyl; and (3) —$CH_2$—C≡C—Y, wherein Y is as defined previously, with the proviso that in compounds of formula (II) wherein $R^1$ is selected from option (1) the $C_1$–$C_6$-alkyl group must be substituted, the method comprising (a) treating a compound selected from the group consisting of

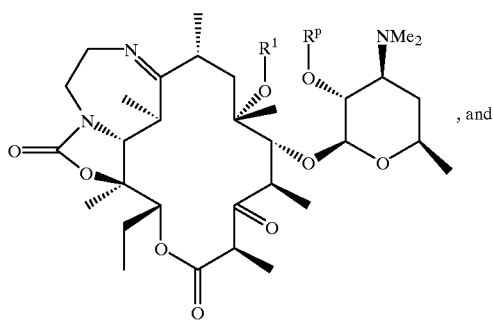

(I)

, and

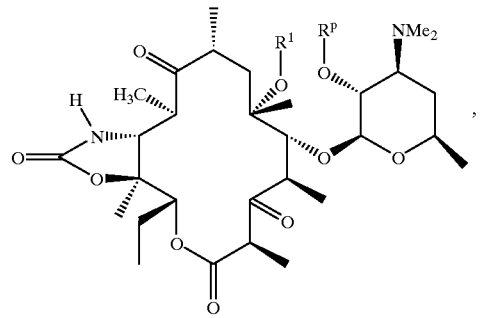

(II)

respectively, with a halogenating reagent, and optionally deprotecting.

11. The process of claim 10 wherein the halogenating reagent is selected from the group consisting of N-fluorobenzenesulfonimide in the presence of base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base, hexachloroethane in the presence of base, $CF_3CF_2CH_2ICl_2$, $SO_2Cl_2$, $SOCl_2$, $CF_3SO_2Cl$ in the presence of base, $Cl_2$, NaOCl in the presence of acetic acid, $Br_2$•pyridine•HBr, $Br_2$/acetic acid, N-bromosuccinimide in the presence of base, LDA/$BrCH_2CH_2Br$, LDA/$CBr_4$, N-Iodosuccinimide in the presence of base, and $I_2$.

12. The process of claim 10 wherein the product is of formula (I), X is F and the halogenating reagent is N-fluorobenzenesulfonimide in the presence of sodium hydride.

13. The process of claim 10 wherein the product is of formula (II), X is F and the halogenating reagent is N-fluorobenzenesulfonimide in the presence of sodium hydride.

14. The process of claim 13 wherein $R^1$ is —$CH_2$—CH═CH—Y and Y is selected from the group consisting of (3-quinolyl), 6-nitro-3-quinolinyl-, phenyl-, 6-tert butoxycarbonylamino-3-quinolinyl-6-amino-3-quinolinyl-, 6-quinolinyl-, 3-(1,8-naphthyridinyl)-, 6-quinoxalinyl-, 6-(dimethylamino)-3-quinolinyl-, 6-(aminosulfonylmethyl)-3-quinolinyl-, 6-(aminocarbonyl)-3-quinolinyl-, 6-(N-methylamino)-3-quinolinyl-,6-(formyl)-3-quinolinyl-, 6-[(hydroxyimino)methyl]-3-quinolinyl-, 6-[aminoimino (methyl)]-3-quinolinyl-, 6-[[(1-methylethylidene) aminoimino]methyl]-3-quinolinyl-, and 3-(5-cyano) pyridinyl-.

\* \* \* \* \*